(12) United States Patent
Ho et al.

(10) Patent No.: US 7,910,603 B2
(45) Date of Patent: Mar. 22, 2011

(54) 3-MONOSUBSTITUTED TROPANE DERIVATIVES AS NOCICEPTIN RECEPTOR LIGANDS

(75) Inventors: Ginny D. Ho, Murray Hill, NJ (US); Deen Tulshian, Lebanon, NJ (US); Shu-Wei Yang, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 131 days.

(21) Appl. No.: 12/338,384

(22) Filed: Dec. 18, 2008

(65) Prior Publication Data

US 2009/0105248 A1 Apr. 23, 2009

Related U.S. Application Data

(62) Division of application No. 11/589,388, filed on Oct. 30, 2006, now Pat. No. 7,479,494.

(60) Provisional application No. 60/731,703, filed on Oct. 31, 2005.

(51) Int. Cl.
*A01N 43/42* (2006.01)
*A61K 31/44* (2006.01)

(52) U.S. Cl. ...................................... 514/304

(58) Field of Classification Search ............... 514/235.2, 514/274, 299; 544/316, 127; 546/112
See application file for complete search history.

(56) References Cited

U.S. PATENT DOCUMENTS

| | | | |
|---|---|---|---|
| 6,262,066 B1 | 7/2001 | Tulshian et al. |
| 6,451,816 B1 | 9/2002 | Biedermann et al. |
| 6,455,527 B2 | 9/2002 | Tulshian et al. |
| 6,716,846 B2 | 4/2004 | Tulshian et al. |
| 6,727,254 B2 | 4/2004 | Tulshian et al. |
| 7,094,784 B2 | 8/2006 | Tulshian et al. |
| 7,485,650 B2 | 2/2009 | Sawutz et al. |
| 2003/0195185 A1 | 10/2003 | Burnett et al. |
| 2004/0067950 A1 | 4/2004 | Tulshian et al. |

FOREIGN PATENT DOCUMENTS

| WO | WO95/04742 | 2/1995 |
|---|---|---|
| WO | WO97/48397 | 12/1997 |
| WO | WO98/25924 | 6/1998 |
| WO | WO00/06545 | 2/2000 |
| WO | WO03/039469 | 5/2003 |

OTHER PUBLICATIONS

Varty et al., The Journal of pharmacology and experimental therapeutics, 2008, vol. 326, No. 2, pp. 672-682.*
Ciccocioppo et al., physiology & behavior, vol. 79 (2003), pp. 121-128.*
Rouget et al., British journal of pharmacology, vol. 141, (2004), pp. 1077-1083.*
Zambello et al., Progress in Neuro-Psychopharmacology & Biological Psychiatry, vol. 32 (2008), pp. 651-661.*
Mcleod et al., European journal of pharmacology, vol. 630 (2010), pp. 112-120.*
Fu et al., brain research, vol. 1078 (2006), pp. 212-218.*
International Search Report for International Application No. PCT/US2006/041925 dated Feb. 12, 2007.
McLeod, Robbie L., et al.; "Antitussive Effect of Nociceptin/Orphanin FQ in Experimental Cough Models"; Pulmonary Pharmacology & Therapeutics; 15:213-216 (2002).
Written Opinion for International Application No. PCT/US2006/041925 (Apr. 2008).

* cited by examiner

*Primary Examiner* — Janet L Andres
*Assistant Examiner* — Niloofar Rahmani
(74) *Attorney, Agent, or Firm* — Eric A. Meade; Krishna G. Banerjee

(57) ABSTRACT

Compounds of the formula or a pharmaceutically acceptable salt thereof, wherein
$R^1$ is aryl, arylalkyl, heteroaryl, heteroarylalkyl, cycloalkyl, cycloalkylalkyl, heterocycloalkyl, heterocycloalkylalkyl or alkyl, all optionally substituted;
$R^2$ is H; or aryl, arylalkyl, heteroaryl, heteroarylalkyl, cycloalkyl, cycloalkylalkyl, heterocycloalkyl, heterocycloalkylalkyl or alkyl, all optionally substituted;
$R^3$ is aryl, heteroaryl, cycloalkyl or heterocycloalkyl, all optionally substituted;
X is a bond, $-(CH_2)_m-N(R^7)-(CH_2)_n-$, $-(CH_2)_m-O-(CH_2)_n-$, $-(CH_2)_m-S-(CH_2)_n-$, $-C(O)-$, $-CH(OH)-$, $-C(O)N(R^7)-$, $-C(O)N(R^7)$-alkylene or $-N(R^7)C(O)-$;
$R^7$ is H or alkyl; and
m and n are each 0-6, provided that the sum of m and n is 0-6;
or a pharmaceutically acceptable salt or solvate thereof, pharmaceutical compositions thereof, and the use of said compounds in the treatment of cough, pain, anxiety, asthma, depression, alcohol abuse, urinary incontinence and overactive bladder are disclosed.

2 Claims, No Drawings

3-MONOSUBSTITUTED TROPANE DERIVATIVES AS NOCICEPTIN RECEPTOR LIGANDS

CROSS-REFERENCE TO RELATED APPLICATIONS

This Application is a divisional of U.S. application Ser. No. 11/589,388, filed Oct. 30, 2006, now U.S. Pat. No. 7,479,494 B2, which claims the benefit of U.S. Provisional Application Ser. No. 60/731,703, filed Oct. 31, 2005, which is incorporated herein by reference in its entirety.

FIELD OF THE INVENTION

The present invention relates to nociceptin receptor agonist 3-monosubstituted tropane derivatives useful in treating cough, pain, anxiety, asthma, alcohol abuse, depression, urinary incontinence or overactive bladder. Pharmaceutical compositions comprising the compounds and combinations of the claimed compounds with other agents for treating cough, allergy or asthma symptoms are also disclosed.

BACKGROUND

Nociceptin is a seventeen amino acid neuropeptide that has been recently identified as a potent endogenous agonist of the opioid-like receptor NOP (previously termed ORL-1). The NOP receptor is a G-protein coupled receptor with 47% overall homology to the opioid receptors and 64% identical in transmembrane domains. In spite of this homology, classical opioid ligands have very low affinity for this receptor. Activation of the NOP receptor leads to inhibition of adenylyl cyclase activity and modulation of neuronal $K^+$ and $Ca^{+2}$ conductance. It is structurally related to the opioid peptides but does not activate opioid receptors.

Nociceptin and its receptor are widely expressed throughout the central nervous system. Thus, nociceptin is likely to participate in a broad range of physiological and behavioral functions. Reports in literature have implicated its role in cough (see, for example, McLeod et al, *Pulmonary Pharmacology & Therapeutics* (2002), 15, 213-216) as well as in pain, feeding, locomotor activity, alcohol abuse, urinary incontinence, anxiety, stress, cardiovascular functions, sleep disturbance, Parkinson's Disease and Alzheimer's Disease.

3-Substituted 8-azabicyclo-[3.2.1]octanes were disclosed in U.S. Pat. No. 6,262,066 B1, WO 95/04742, WO 97/48397, and WO 98/25924; 3-substituted 8-azabicyclo-[3.2.1]octan-3-ols were disclosed in U.S. Pat. No. 6,727,254 B2.

SUMMARY OF THE INVENTION

Compounds of the present invention are represented by formula I

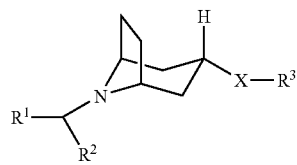

I or a pharmaceutically acceptable salt thereof, wherein
$R^1$ is $R^4$-aryl, $R^4$-arylalkyl, $R^4$-heteroaryl, $R^4$-heteroarylalkyl, $R^4$-cycloalkyl, $R^4$-cycloalkylalkyl, $R^4$-heterocycloalkyl or $R^4$-heterocycloalkylalkyl;

$R^2$ is $R^5$-aryl, $R^5$-arylalkyl, $R^5$-heteroaryl, $R^5$-heteroarylalkyl, $R^5$-cycloalkyl, $R^5$-cycloalkylalkyl, $R^5$-heterocycloalkyl or $R^5$-heterocycloalkylalkyl;

$R^3$ is $R^6$-alkyl, $R^6$-aryl, $R^6$-heteroaryl, $R^6$-cycloalkyl or $R^6$-heterocycloalkyl;

X is a bond, $(C_1\text{-}C_3)$alkylene, $-(CH_2)_m-N(R^7)-(CH_2)_n-$, $-(CH_2)_m-O-(CH_2)_n-$, $-(CH_2)_m-S-(CH_2)_n-$, $-C(O)-$, $-CH(OH)-$, $-C(O)N(R^7)-$, $-C(O)N(R^7)$-alkylene or $-N(R^7)C(O)-$;

n is 0, 1, 2, 3; 4, 5 or 6; m is 0, 1, 2, 3; 4, 5 or 6; provided that the sum of m and n is 0, 1, 2, 3; 4, 5 or 6;

each $R^4$ and $R^5$ is 1 to 3 substituents independently selected from the group consisting of H, halo, alkyl, cycloalkyl, $-CN$, $-CF_3$, $-(CH_2)_p-OR^8$, $-N(R^{10})_2$ and $-(CH_2)_n-N(R^{10})_2$;

$R^6$ is 1 to 3 substituents independently selected from the group consisting of H, halo, alkyl, cycloalkyl, heterocycloalkyl, heterocycloalkylalkyl, $-CN$, cyanoalkyl, $-CF_3$, $-C(O)$alkyl, $-(CH_2)_p-OR^8$, $-COOR^8$, $-N(R^{10})_2$, $-(CH_2)_n-N(R^{10})_2$ and $-C(O)N(R^{10})_2$;

p is 0, 1, 2, 3; 4, 5 or 6;

$R^7$ is H or alkyl;

$R^8$ and $R^9$ are independently selected from the group consisting of H, alkyl, cycloalkyl, haloalkyl, hydroxyalkyl, alkoxy, alkoxyalkyl, aminoalkyl, alkyl-C(O)— and alkyl-C(O)—N($R^7$)—C(O)—; and $R^{10}$ is independently selected from the group consisting of H and alkyl.

In another aspect, the invention relates to a pharmaceutical composition comprising at least one compound of formula I and a pharmaceutically acceptable carrier.

The compounds of the present invention are agonists of the NOP receptor, and therefore, in another aspect, the invention relates to a method of treating pain, anxiety, cough, asthma, alcohol abuse, depression, urinary incontinence or overactive bladder, comprising administering to a mammal in need of such treatment an effective amount of at least one compound of formula I.

In another aspect, the invention relates to a method of treating cough, comprising administering to a mammal in need of such treatment an effective amount of a combination of: (a) at least one compound of formula I; and (b) one or more additional agents for treating cough, allergy or asthma symptoms selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists.

In still another aspect, the invention relates to a pharmaceutical composition comprising at least one compound of formula I and one or more additional agents selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists.

In another aspect, the invention relates to a method of treating urinary incontinence (UI) or overactive bladder comprising administering to a mammal in need of such treatment an effective amount of a combination of: (a) at least one compound of formula I; and (b) one or more agents useful for treating UI or overactive bladder.

In still another aspect, the invention relates to a pharmaceutical composition comprising at least one compound of formula I and one or more agents useful for treating UI or overactive bladder.

DETAILED DESCRIPTION OF THE INVENTION

Referring to formula I, above, preferred compounds of the invention are those wherein $R^1$ is $R^4$-phenyl and $R^2$ is $R^5$-phenyl, wherein $R^4$ and $R^5$ are independently selected from the group consisting of H, halo and alkyl. More preferably, $R^1$ is $R^4$-phenyl wherein $R^4$ is one halo atom, and $R^2$ is $R^5$-phenyl wherein $R^5$ is H or one halo atom. The preferred halo atom for $R^4$ and $R^5$ is chlorine. The $R^4$ and $R^5$ substituents are preferably in the 2-position in the phenyl ring.

X is preferably a bond, $-(CH_2)_m-N(R^7)-(CH_2)_n-$ wherein $R^7$ is H, m is 0 and n is 0 or 1, or $-C(O)N(R^7)-$ wherein $R^7$ is H. More preferably, X is a bond.

$R^3$ is preferably $R^6$-aryl, $R^6$-heteroaryl or $R^6$-heterocycloalkyl, wherein aryl is preferably phenyl, heteroaryl is preferably pyridyl, pyrimidyl, imidazolyl or benzimidazolyl, and heterocycloalkyl is preferably piperidinyl or morpholinyl. Preferred $R^6$ substituents are H, halo, alkyl, OH, $-OCH_3$ (i.e., $-(CH_2)_n-OR^8$ wherein n is 0 or 1 and $R^8$ is H), hydroxyalkyl (i.e., $-(CH_2)_n-OR^8$ wherein n is 1 to 6 and $R^8$ is H), cycloalkyl and heterocycloalkylalkyl (e.g., piperidinylmethyl). More preferably, $R^6$ is one substituent selected from H, halo, alkyl, OH and $-OCH_3$.

Preferred compounds of the invention are those described below in Examples 1, 2, 8, 12, 13, 14, 16, 19, 20, 21, 23, 28, 29 and 62.

A preferred indication for compounds of formula I is the treatment of cough.

As used herein, the following terms are used as defined below unless otherwise indicated:

halo represents fluoro, chloro, bromo and iodo;

alkyl (including, for example, the alkyl portions of arylalkyl) represents straight and branched carbon chains and contains from one to six carbon atoms;

alkylene represents a divalent straight or branched alkyl chain, e.g., ethylene $(-CH_2-)_2$ or propylene $(-CH_2CH_2CH_2-)$;

cycloalkyl represents a non-aromatic mono- or multicyclic ring system comprising about 3 to about 10 carbon atoms, preferably about 5 to about 10 carbon atoms. Preferred cycloalkyl rings contain about 3 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantly and the like;

aryl (including the aryl portion of arylalkyl) represents a carbocyclic group containing from 6 to 15 carbon atoms and having at least one aromatic ring (e.g., aryl is a phenyl or naphthyl ring), with all available substitutable carbon atoms of the carbocyclic group being intended as possible points of attachment;

heteroaryl represents cyclic aromatic groups of 5 or 6 atoms or bicyclic groups of 9 to 10 atoms having 1, 2 or 3 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. Nitrogen atoms can form an N-oxide. All regioisomers are contemplated, e.g., 2-pyridyl, 3-pyridyl and 4-pyridyl. Typical 6-membered heteroaryl groups are pyridyl, pyrimidinyl, pyrazinyl, pyridazinyl and the N-oxides thereof. Typical 5-membered heteroaryl rings are furyl, thienyl, pyrrolyl, thiazolyl, isothiazolyl, imidazolyl, pyrazolyl and isoxazolyl. Bicyclic groups typically are benzo-fused ring systems derived from the heteroaryl groups named above, e.g. benzimidazolyl, quinolyl, phthalazinyl, quinazolinyl, benzofuranyl, benzothienyl and indolyl. The heteroaryl ring can be substituted with 1-3 $R^4$, $R^5$ or $R^6$ groups, wherein any of the available substitutable carbon or nitrogen atoms in said heteroaryl group may be optionally and independently substituted;

heterocycloalkyl represents a saturated carbocylic ring containing from 3 to 15 carbon atoms, preferably from 4 to 6 carbon atoms, which carbocyclic ring is interrupted by 1 to 3 hetero atoms selected from $-O-$, $-S-$, $-SO-$, $-SO_2$ or $-NH-$; examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl. The heterocycloalkyl ring can be substituted with 1-3 $R^4$, $R^5$ or $R^6$ groups, wherein any of the available substitutable carbon or nitrogen atoms in said heterocycloalkyl group may be optionally and independently substituted Claim 1 does not include compounds known by the skilled artisan to be unstable.

The compounds of the invention can be in purified or isolated form. The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., $R^4$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyl-oxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a compound of formula I contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)-ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of formula I incorporates an amine functional group, a prodrug can be formed by the replacement of a hydrogen atom in the amine group with a group such as, for example, R"-carbonyl, R"O-carbonyl, NR"R'''-carbonyl where R" and R''' are each independently $(C_1-C_{10})$alkyl, $(C_3-C_7)$ cycloalkyl, benzyl, or R"-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may also exist as, or optionally converted to, a solvate. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of Formula I, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Polymorphic forms of the compounds of Formula I, and of the salts, solvates, esters and prodrugs of the compounds of Formula I, are intended to be included in the present invention.

Compounds of the invention can be prepared by known methods from starting materials either known in the art or prepared by methods known in the art. Scheme 1 shows a typical reaction scheme for preparing compounds of formula I wherein $R^1$ and $R^2$ are as defined above, X is a bond and $R^{3a}$ is $R^6$-phenyl or $R^6$-heteroaryl joined to the tropane ring through a ring carbon (e.g., $R^6$—(2-pyrimidyl) or $R^6$-pyridyl).

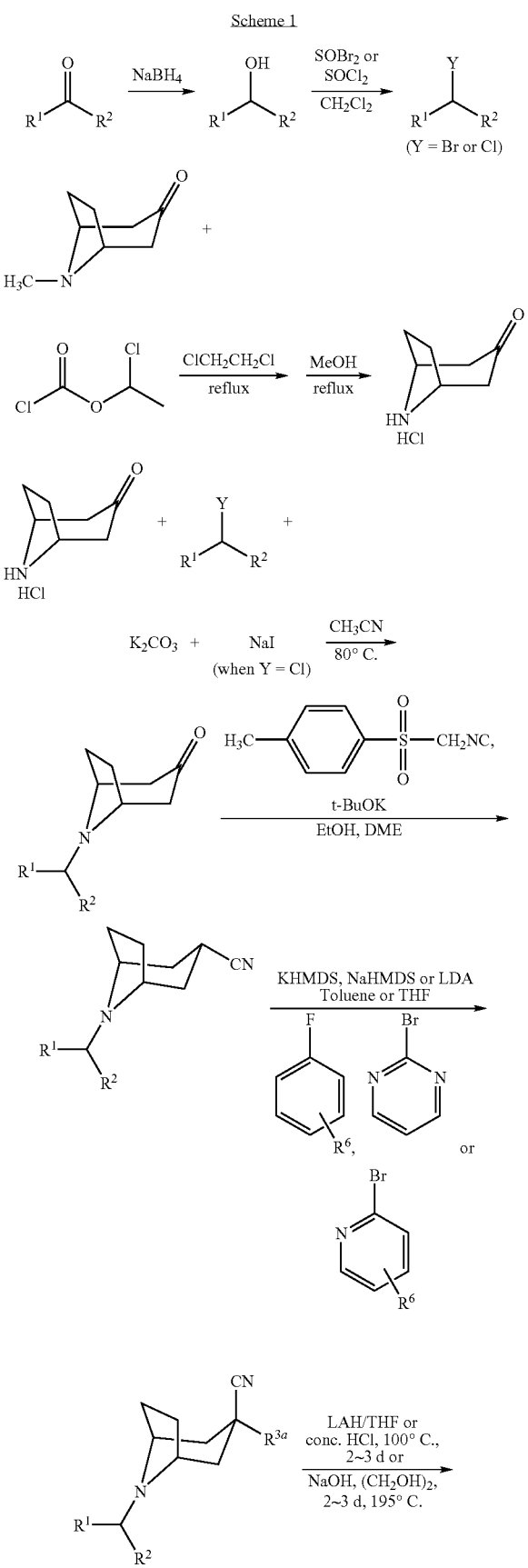

-continued

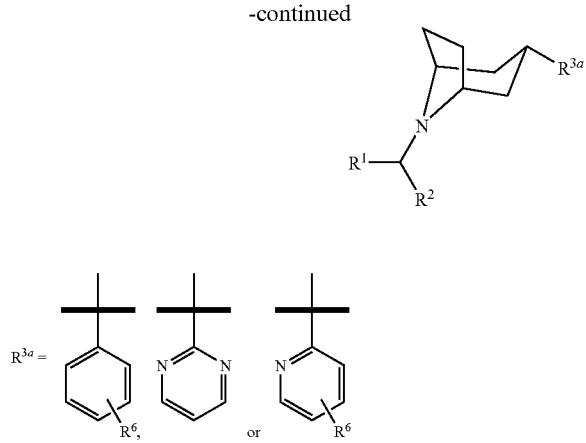

Compounds of formula I in Scheme 1 wherein $R^{3a}$ is pyridinyl can be converted to the corresponding piperidinyl compounds by hydrogenation with an agent such as $PtO_2$.

Scheme 2 shows a typical reaction scheme for preparing compounds of formula I wherein $R^1$ and $R^2$ are as defined above, X is a bond and $R^{3b}$ is $R^6$-heteroaryl or $R^6$-heterocycloalkyl joined to the tropane ring through a ring nitrogen (e.g., $R^6$—(pyrazol-1-yl) or $R^6$-piperidinyl). The mesylate intermediate is also used to prepare compounds of formula I wherein $R^1$ and $R^2$ are as defined above, X is —N($R^7$)—$(CH_2)_n$— wherein $R^7$ is H and n is 0, and $R^{3c}$ is, for example, $R^6$-pyridyl or $R^6$-pyrimidyl, where the pyridyl or pyrimidyl ring is joined through a ring carbon atom. Also, the tropane alcohol intermediate can be converted to the compound wherein X is —O— and $R^{3d}$ is $R^6$-phenyl or $R^{3e}$ is $R^6$-pyrimidyl; the amino-tropane intermediate can be converted to a compound wherein —X—$R^3$ is —NHC(O)—$R^3$, which can be reduced to obtain the corresponding —NH—$CH_2$—$R^3$ compound.

Scheme 2

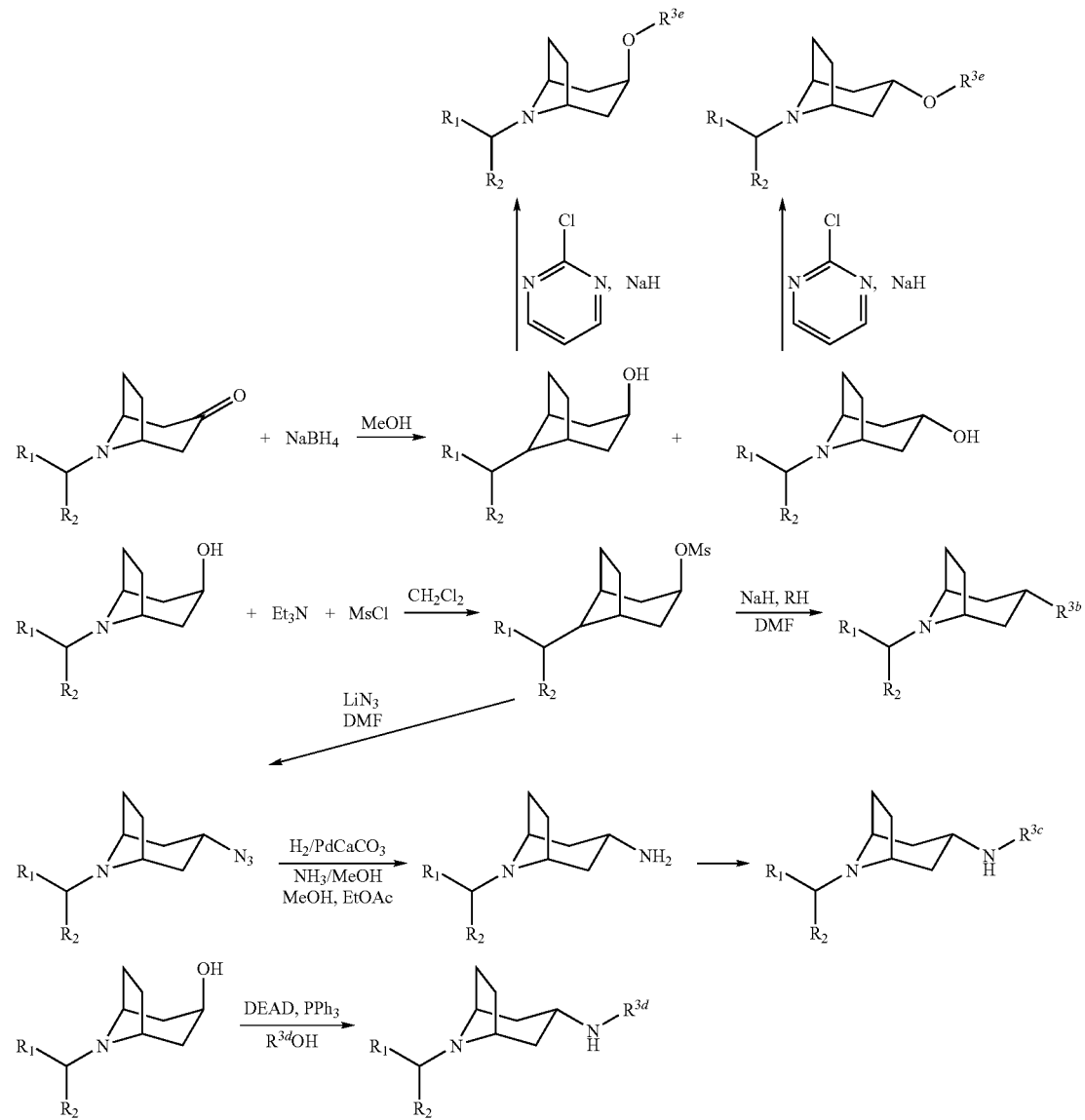

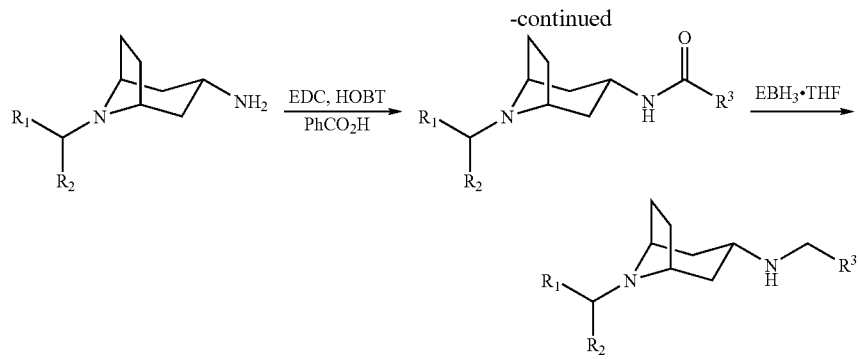

Scheme 3 shows a typical reaction scheme for preparing compounds of formula I wherein $R^1$, $R^2$ and $R^3$ are as defined above and X is $-C(O)N(R^7)-$, which can be reduced to compounds wherein X is $-CH_2-N(R^7)-$.

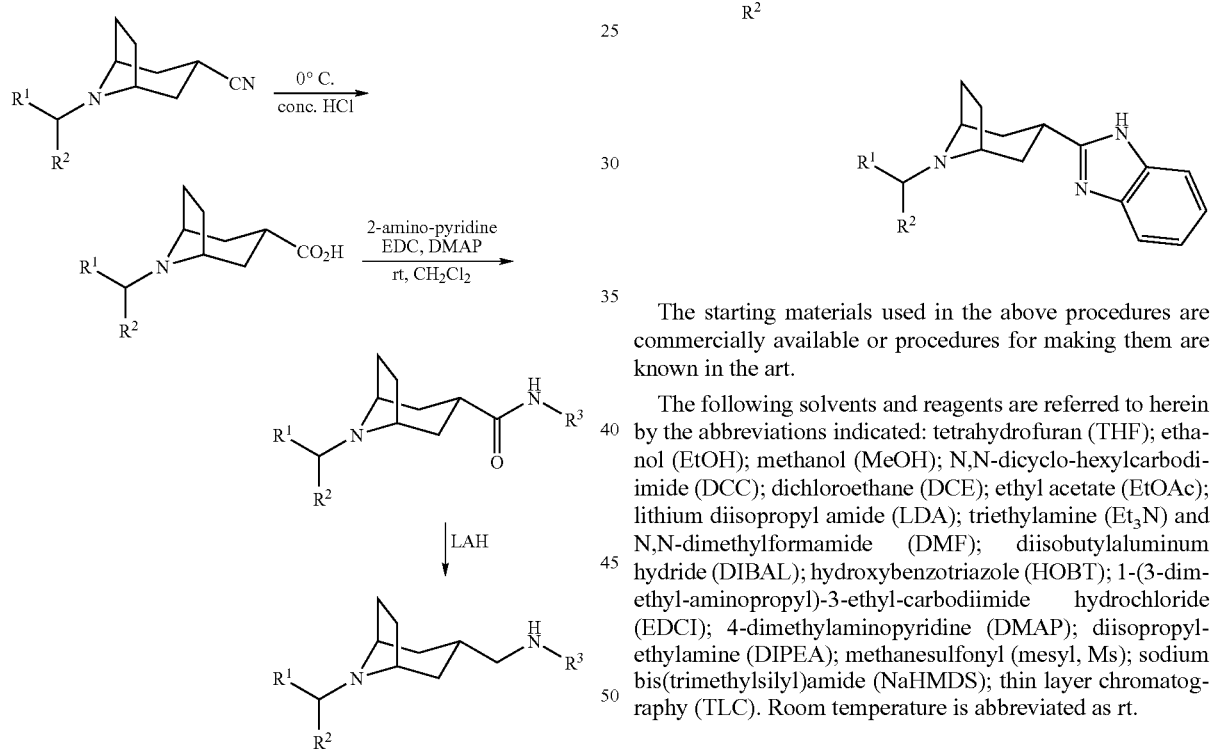

Scheme 4 shows a reaction scheme for preparing compounds of formula I wherein $R^1$ and $R^2$ are as defined above, X is a bond, and $R^3$ is benzimidazolyl.

The starting materials used in the above procedures are commercially available or procedures for making them are known in the art.

The following solvents and reagents are referred to herein by the abbreviations indicated: tetrahydrofuran (THF); ethanol (EtOH); methanol (MeOH); N,N-dicyclo-hexylcarbodiimide (DCC); dichloroethane (DCE); ethyl acetate (EtOAc); lithium diisopropyl amide (LDA); triethylamine ($Et_3N$) and N,N-dimethylformamide (DMF); diisobutylaluminum hydride (DIBAL); hydroxybenzotriazole (HOBT); 1-(3-dimethyl-aminopropyl)-3-ethyl-carbodiimide hydrochloride (EDCI); 4-dimethylaminopyridine (DMAP); diisopropylethylamine (DIPEA); methanesulfonyl (mesyl, Ms); sodium bis(trimethylsilyl)amide (NaHMDS); thin layer chromatography (TLC). Room temperature is abbreviated as rt.

EXAMPLE 1

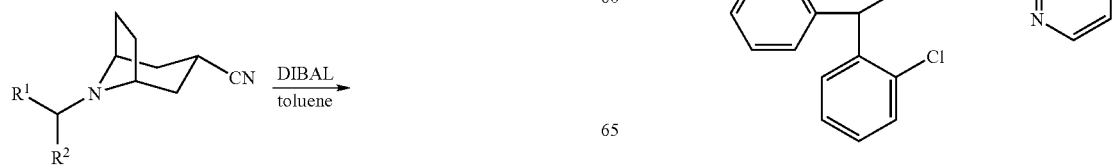

Step 1:

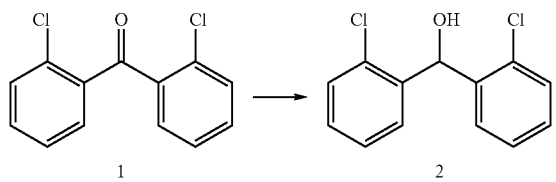

NaBH$_4$ (1.5 g, 39.82 mmol) was added to a solution of 2,2'-dichlorobenzo-phenone 1 (5 g, 19.9 mmol) in MeOH (40 ml) at rt. After stirring at rt for 2 h, the mixture was quenched with H$_2$O, neutralized with 1N HCl followed by evaporation of MeOH. The residue was extracted with EtOAc, washed with brine, dried (MgSO$_4$) and concentrated to give the desired compound 2 (5 g) as white solid which was used for next step reaction without purification. $^1$H NMR (CDCl$_3$) δ 7.45 (m, 4H), 7.35 (m, 4H), 6.60 (d, 1H), 2.58 (d, 1H, OH).

Step 2:

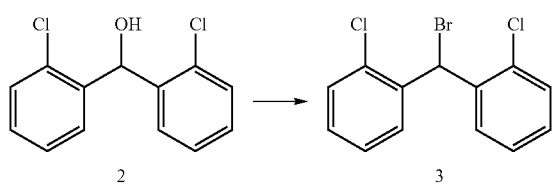

The product of Step 1 (20.36 g, 80.47 mmol) in CH$_2$Cl$_2$ was treated with SOBr$_2$ (30.11 g, 144.85 mmol) at 0° C. After stirring at rt overnight, the mixture was quenched with ice and NaHCO$_3$ (aq.), extracted with CH$_2$Cl$_2$, dried, filtered and concentrated to produce the desired compound 3 (23.6 g). $^1$H NMR (CDCl$_3$) δ 7.6 (d, 2H), 7.4 (d, 2H), 7.13 (m, 4H), 7.0 (s, 1H).

Step 3:

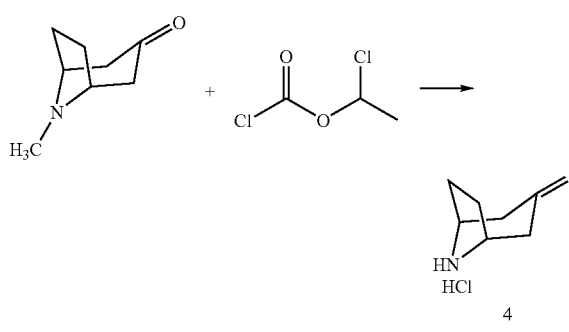

A solution of tropinone (10 g, 71.84 mmol) in DCE (200 ml) was added α-chloroethyl chloroformate (15.4 g, 108 mmol) dropwise at 0° C. The mixture was then heated at reflux for 2 h. Solvent was evaporated to give a brown residue. The residue was dissolved in MeOH (200 ml) and heated at reflux for 2 h. The MeOH was evaporated to give a solid which was stirred in EtOAc, filtered and washed with ether to give the desired compound 4 (7 g). Crude product was used for the next step without further purification. $^1$H NMR (CDCl$_3$) δ 4.45 (s, br, 2H), 3.35 (dd, 2H), 2.58 (d, 2H), 2.49 (dd, 2H), 2.0 (m, 2H).

Step 4:

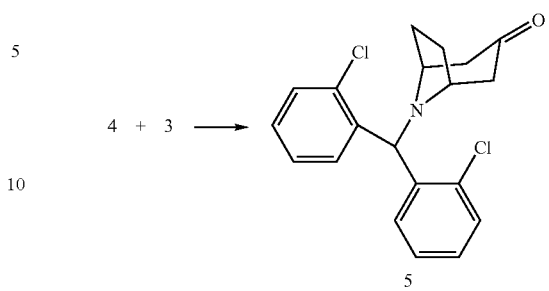

A mixture of 4 (26 g, 161 mmol), 3 (53 g, 168 mmol) and K$_2$CO$_3$ (110 g, 796 mmol) in anhydrous CH$_3$CN (410 ml) was heated at 80° C. Reaction progress was monitored by $^1$H NMR analysis. ~79% conversion was observed after 87 h. The reaction mixture was cooled to rt, diluted with CH$_2$Cl$_2$, filtered and concentrated. Purification of the residue by SiO$_2$ chromatography (4-7% EtOAc/hexane) gave the desired compound 5. $^1$H NMR (CDCl$_3$) δ 7.9 (d, 2H), 7.3 (m, 4H), 7.2 (m, 2H), 5.7 (s, 1H), 3.35 (s, br, 2H), 2.7 (dd, 2H), 2.3 (m, 2H), 2.2 (d, 2H), 1.65 (dd, 2H).

Step 5:

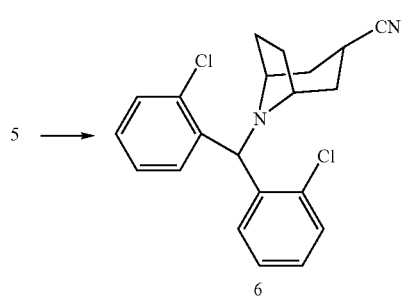

Potassium tert-butoxide (232 g) was added slowly to a stirred solution of 5 (300 g) and tosylmethyl isocyanide (211 g) in anhydrous 1,2-dimethoxyethane (3.5 l) and absolute EtOH (240 ml) under N$_2$ at −40° C. The mixture was slowly warmed to rt and stirred at rt overnight. The mixture was filtered and washed with EtOAc. Most of the solvent in the filtrate was evaporated in vacuo (bath temperature <40° C.) to give a suspension which was filtered and washed with ether to give 6 (158 g). LC/ESI-MS m/z=371 (C$_{21}$H$_{20}$Cl$_2$N$_2$.H$^+$).

Step 6:

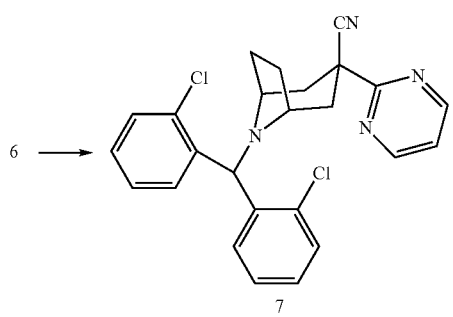

LDA was freshly generated from diisopropyl amine (2.27 ml, 16.15 mmol) and n-BuLi (2.5 M, 6.46 ml, 16.15 mmol) in THF (25 ml). The LDA solution was treated with a solution of 6 in THF (25 ml) dropwise at −40° C., stirred for 2 h and 2-chloro-pyrimidine (1.85 g, 16.15 mmol) was added. The mixture was slowly warmed to rt, stirred at rt overnight, quenched with water, extracted with EtOAc, dried (MgSO$_4$) and concentrated. Purification of the residue by SiO$_2$ chromatography (1:4 EtOAc/hexane) gave 7 (3 g). LC/ESI-MS m/z=449 (C$_{25}$H$_{22}$Cl$_2$N$_4$. H$^+$).

Step 7:

A mixture of 7 (200 mg) and conc. HCl (2 ml) was heated at 100° C. in a sealed tube for 3 days, cooled to 0° C., neutralized with aqueous NaOH solution, extracted with EtOAc, dried (MgSO$_4$) and concentrated. Purification of the residue by SiO$_2$ chromatography (0-50% EtOAc/hexane) gave the title compound (110 mg). LC/ESI-MS m/z=424 (C$_{24}$H$_{23}$Cl$_2$N$_3$.H$^+$).

EXAMPLES 2 AND 3

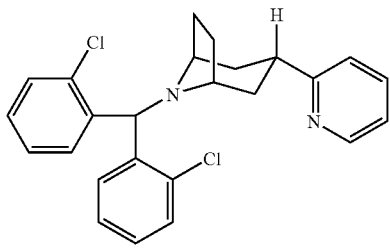

Ex. 2

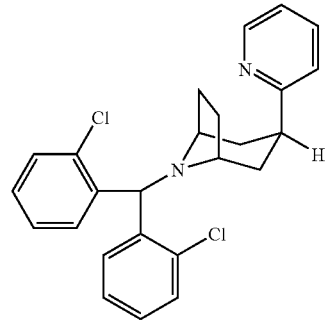

Ex. 3

Step 1:

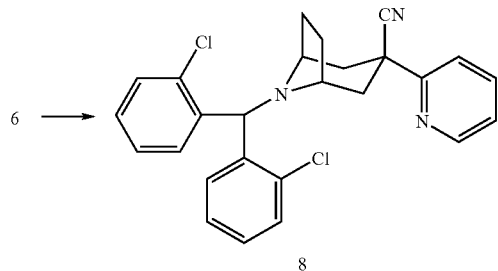

To a stirred solution of 6 (20 g, 53.9 mmol) in THF (100 ml) was added NaHMDS/THF (40.4 ml, 2M) dropwise at −78° C. under N$_2$. The solution was stirred at −78° C. for ~1 hr, then 2-bromopyridine (17 g, 154 mmol) in THF was added dropwise. After stirring for another hour at this temperature, the reaction flask was moved to a CH$_3$CN/dry ice bath. The reaction mixture was slowly warmed to rt, stirred at rt overnight, quenched with sat. aq. NH$_4$Cl at −78° C., warmed to rt, and extracted with EtOAc. The combined organic layers were dried over Na$_2$SO$_4$, filtered, and evaporated to dryness. The residue was washed with ether several times to give the desired compound 8 (19.1 g) which was used in the next reaction without further purification. LC/ESI-MS: m/z 448 (C$_{26}$H$_{23}$Cl$_2$N$_3$. H$^+$).

Step 2:

A mixture of 8 (5 g), NaOH (20 g), and ethylene glycol (40 ml) was stirred and heated to 200° C. under N$_2$ atmosphere for two to three days. After the reaction was complete, the mixture was cooled to rt and dissolved in 1 N HCl solution. The suspension was partitioned with CH$_2$Cl$_2$ under basic conditions. The organic layer was dried over Na$_2$SO$_4$, filtered, and evaporated to dryness. Purification of the residue by SiO$_2$ chromatography (EtOAc/hexane) gave Example 2 (~4.3 g), LC/ESI-MS: m/z 423 (C$_{25}$H$_{24}$Cl$_2$N$_2$.H$^+$) and Example 3, LC/ESI-MS: m/z 423 (C$_{25}$H$_{24}$Cl$_2$N$_2$.H$^+$).

EXAMPLES 4 AND 5

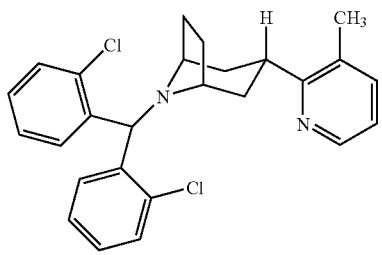

Ex. 4

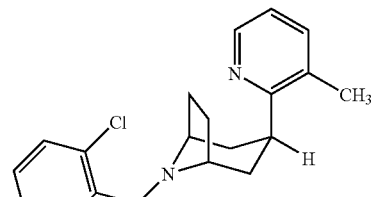

Ex. 5

Step 1:

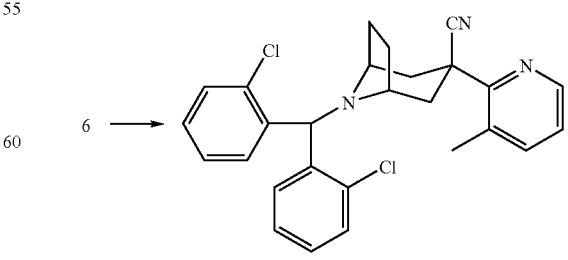

Compound 9 was prepared according to the procedure described in Example 2, Step 1, using 6, NaHMDS and 2-bromo-3-methylpyridine. LC/ESI-MS: m/z 462 ($C_{27}H_{25}Cl_2N_3.H^+$).

Step 2:
To a stirred solution of 9 (1.92 g, 4.156 mmol) in THF was added 1 M LiALH$_4$/THF solution (4.57 ml, 4.57 mmol) dropwise at rt under N$_2$. The mixture was stirred at 50° C. for 1 h. After cooling to rt, the following solutions were added sequentially: 190 µl water, 570 µl 15% NaOH, and 190 µl water. The mixture was stirred, filtered, and evaporated to dryness. Purification of the residue by SiO$_2$ chromatography (EtOAc/hexane) gave Example 4 (~370 mg), LC/ESI-MS: m/z 437 ($C_{26}H_{26}Cl_2N_2.H^+$) and Example 5, LC/ESI-MS: m/z 437 ($C_{26}H_{26}Cl_2N_2.H^+$).

EXAMPLES 6 AND 7

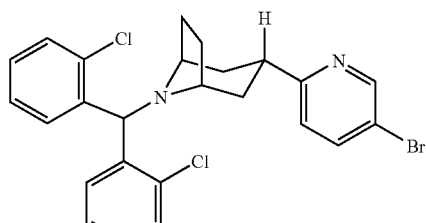

Ex. 6

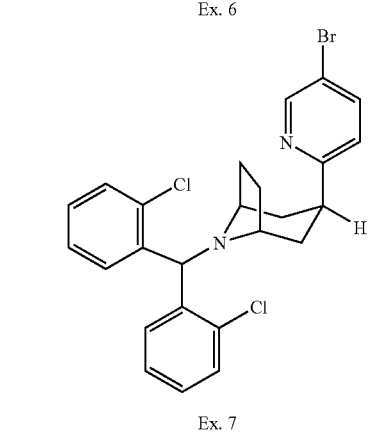

Ex. 7

Step 1:

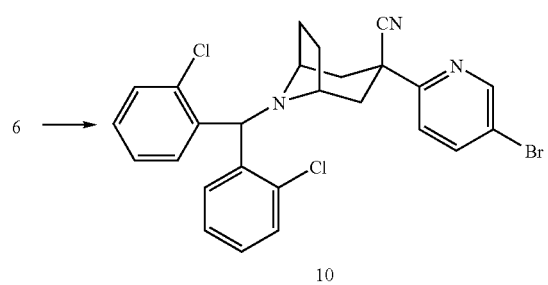

10

Compound 10 was prepared according to the procedure described in Example 2, Step 1, using 6, NaHMDS and 2,5-dibromopyridine. LC/ESI-MS m/z=528 ($C_{26}H_{22}BrCl_2N_3.H^+$).

Step 2:
A mixture of 10 (210 mg) and conc. HCl (1.5 ml) was heated at 100° C. in a sealed tube for 3 days, cooled to rt, neutralized with aqueous NaOH solution, extracted with EtOAc, dried (MgSO$_4$) and concentrated. Purification of the residue by SiO$_2$ chromatography (0-50% EtOAc/hexane) gave Example 6, LC/ESI-MS m/z=503 ($C_{25}H_{23}BrCl_2N_2.H^+$) and Example 7, LC/ESI-MS: m/z 503 ($C_{25}H_{23}BrCl_2N_2.H^+$).

EXAMPLE 8

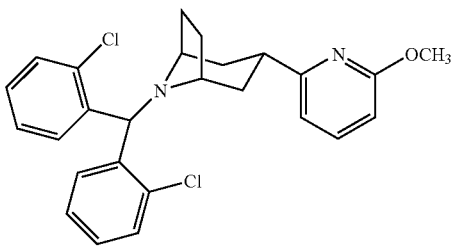

Step 1:

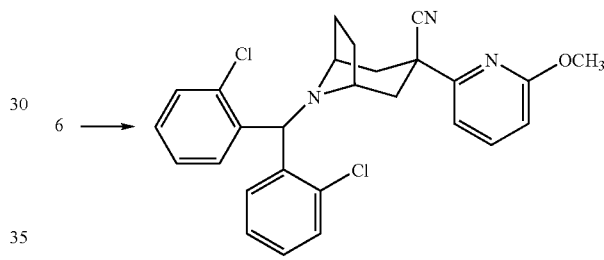

11

Compound 11 was prepared according to the procedure described in Example 2, Step 1, using 6, NaHMDS and 2-bromo-6-methoxypyridine. LC/ESI-MS: m/z 478 ($C_{27}H_{25}Cl_2N_3O.H^+$).

Step 2:
To a stirred solution of 11 (21 mg, 0.044 mmol) in THF, was added 1 M LiALH$_4$/THF solution (132 µl, 0.132 mmol) dropwise at 0° C. under N$_2$. The mixture was stirred at 60° C. overnight. After cooling to rt, the following solutions were added sequentially: 2 µl water, 6 µl 15% NaOH, and 2 µl water. The mixture was stirred, filtered, and evaporated to dryness. Purification of the residue by SiO$_2$ chromatography (0-40% EtOAc/hexane) gave the title compound (5 mg). ESI-MS: m/z 453 ($C_{26}H_{26}Cl_2N_2O.H^+$).

EXAMPLE 9

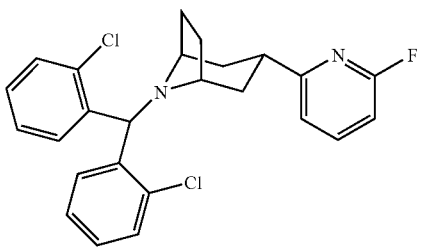

Step 1:

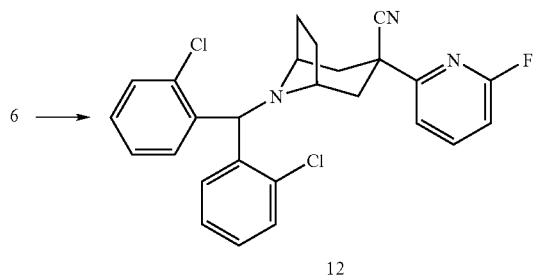

6 →

12

To a stirred solution of 6 (371 mg, 1 mmol) in THF was added NaHMD/THF (750 µl, 2M) dropwise at −78° C. under $N_2$. The solution was stirred at −78° C. for ~0.5 hr, and then 2,6-difluoropyridine in THF was added dropwise. After stirring for at least 6 h at this temperature, the reaction mixture was slowly warmed to rt, and stirred over the weekend. The mixture was cooled to −78° C., quenched with sat. aq. $NH_4Cl$, warmed to rt and partitioned between aq. $NH_4Cl$ solution and EtOAc-hexane (1:1). The combined organic layers were dried over $Na_2SO_4$, filtered, and evaporated to dryness. Purification of the residue by $SiO_2$ chromatography gave 12 (194 mg). LC/ESI-MS: m/z 466 ($C_{26}H_{22}Cl_2FN_3.H^+$).

Step 2:

To a stirred solution of 12 (69.5 mg, 0.149 mmol) in THF was added 1 M $LiAlH_4$/THF solution (149 µl, 0.149 mmol) dropwise at rt under $N_2$. The mixture was stirred at rt overnight. The following solutions were added sequentially: 5 µl water, 15 µl 15% NaOH, and 5 µl water. The mixture was stirred, filtered, and evaporated to dryness. Purification of the residue by $SiO_2$ chromatography (0-100% EtOAc/hexane) gave the title compound (14 mg). LC/ESI-MS: m/z 441 ($C_{25}H_{23}Cl_2FN_2.H^+$).

Step 1:

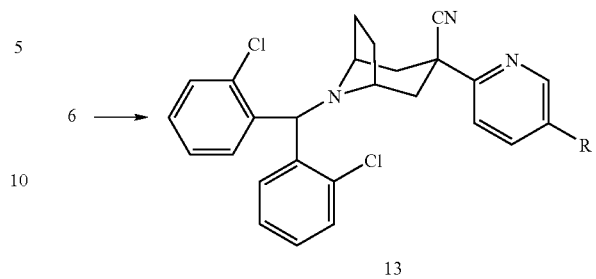

6 →

13

To a stirred solution of 6 (3336 mg, 9 mmol) in THF was added NaHMDS/THF (6750 µl, 2M, 13.5 mmol) dropwise at −78° C. under $N_2$. The solution was stirred at −78° C. for ~0.5 h, and then 2-bromo-5-fluoropyridine (5000 mg, 28.4 mmol) in THF was added dropwise. After stirring for at least 8 h at this temperature, the reaction mixture was slowly warmed to rt and stirred overnight. The mixture was cooled to −78° C., quenched with sat. aq. $NH_4Cl$, warmed to rt and partitioned between aq. $NH_4Cl$ solution and EtOAc. The combined organic layers were dried over $Na_2SO_4$, filtered, and evaporated to dryness. Purification of the residue by $SiO_2$ chromatography (EtOAc/hexane) gave 13 (1650 mg). ESI-MS: m/z 466 ($C_{26}H_{22}Cl_2FN_3$, $H^+$).

Step 2:

A mixture of 13 (67 mg), NaOH (400 mg), and ethylene glycol (4 ml) in a sealed tube was stirred and heated to 150° C. overnight. After cooling to rt, the mixture was added to $H_2O$ and EtOAc. The organic layer was washed with brine, dried over $Na_2SO_4$, filtered, and evaporated to dryness. Purification of the residue by $SiO_2$ chromatography (0-100% EtOAc/hexane) gave Example 10 (~2 mg), ESI-MS: m/z 441 ($C_{25}H_{23}Cl_2FN_2.H^+$) and Example 11 (5 mg), LC/ESI-MS: m/z 439 ($C_{25}H_{24}Cl_2N_2O.H^+$).

EXAMPLE 12

EXAMPLES 10 AND 11

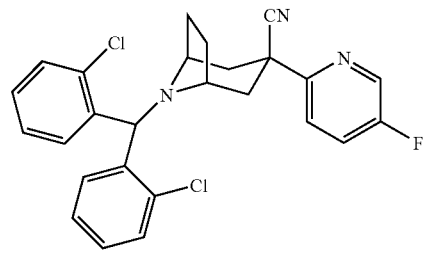

Ex. 10

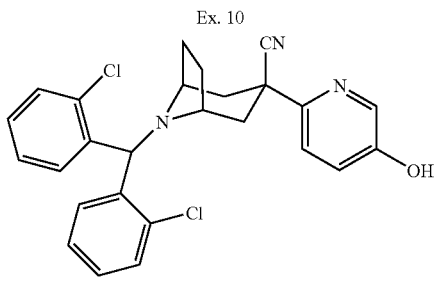

Ex. 11

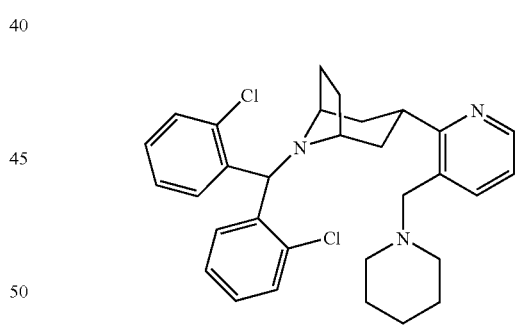

Step 1:

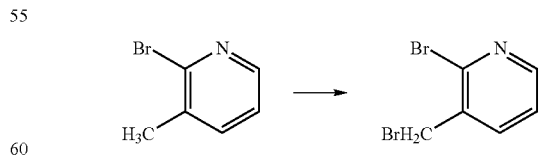

A mixture of 2-bromo-3-methylpyridine (1114 µl, 10 mmol), NBS (1780 mg, 10 mmol), and benzoyl peroxide (45 mg) in $CCl_4$ was refluxed for 3 h. After cooling to rt, the suspension was filtered. Purification of the residue by $SiO_2$ chromatography (EtOAc/hexane) gave the desired compound (600 mg). ESI-MS: m/z 250, 252, and 254 ($C_6H_5Br_2N.H^+$)

Step 2:

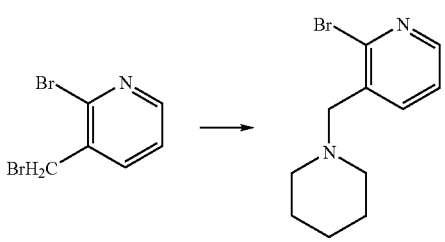

To a solution of the product of Step 1 (595 mg, 2.36 mmol) in DMF was added piperidine (205 mg, 2.4 mmol) and $K_2CO_3$ (979 mg, 7.08 mmol), sequentially. The mixture was stirred at rt overnight, quenched with ice-water and then partitioned with ether. The organic layer was dried over $Na_2SO_4$, filtered, and concentrated. Purification of the residue by $SiO_2$ chromatography (0-50% EtOAc/hexane) gave the desired compound (~450 mg). $C_{11}H_{15}BrN_2$, LC/ESI-MS: m/z 255 and 257 ($C_{11}H_{15}BrN_2.H^+$)

Step 3:

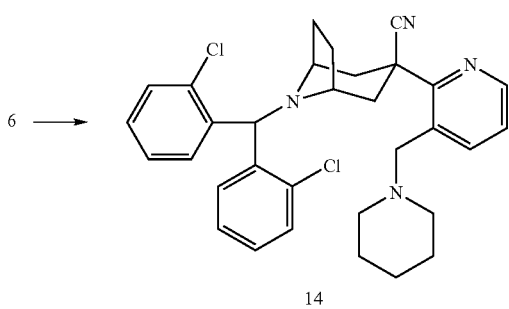

14

Compound 14 was prepared according to the procedure described in Example 2, Step 1, using 6, NaHMDS and the product of Step 2. LC/ESI-MS: m/z 545 ($C_{32}H_{34}Cl_2N_4.H^+$).

Step 4:

14 and $LiAlH_4$ were used according to the procedure described in Example 9, Step 2, to obtain the title compound. LC/ESI-MS: m/z 520 ($C_{31}H_{35}Cl_2N_3.H^+$).

EXAMPLE 13

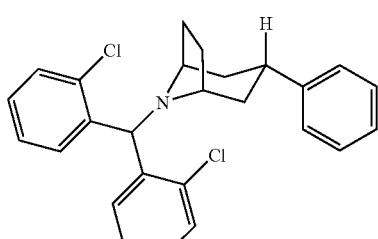

Step 1:

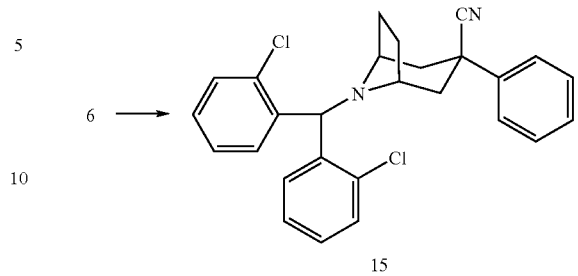

15

To a mixture of 6 (580 mg) and fluorobenzene (~1.5 ml) was added potassium bis(trimethylsilyl)amide (580 mg) in fluorobenzene (~2.5 ml) under $N_2$. The mixture was stirred for 10 min, then heated in a microwave at 100° C. for 18 min. After cooling to rt, the mixture was quenched with saturated aq. $NH_4Cl$ and partitioned with EtOAc. The organic layer was dried over $Na_2SO_4$, filtered, and concentrated. The residue was washed with ether to give 15 (~450 mg). LC/ESI-MS: m/z 447 ($C_{27}H_{24}Cl_2N_2$).

Step 2:

To a stirred solution of 15 (310 mg, 0.693 mmol) in THF was added 1 M $LiALH_4$/THF solution (693 μl, 0.693 mmol) dropwise at rt under $N_2$. The mixture was warmed to 60° C. and stirred overnight. The following solutions were added sequentially: 50 μl water, 150 μl 15% NaOH, and 50111 water. The mixture was stirred, filtered, and evaporated to dryness. Purification of the residue by $SiO_2$ chromatography (0-50% EtOAc/hexane) gave the title compound (~80 mg). LC/ESI-MS: m/z 422 ($C_{26}H_{25}Cl_2N.H^+$).

EXAMPLE 14

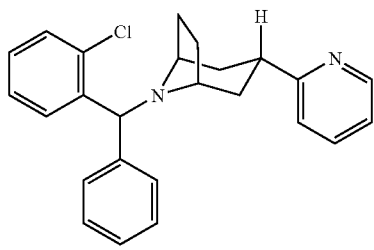

Step 1:

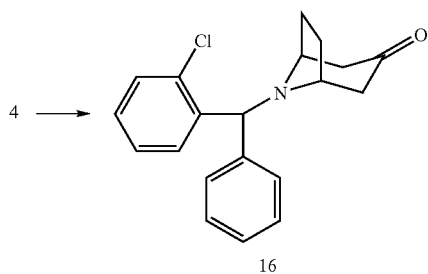

16

Compound 16 was prepared according to the procedure described in Example 1, Step 4, using 4,1-chloro-2-(chlorophenylmethyl)benzene and $K_2CO_3$. $^1$H NMR (CDCl$_3$) δ 7.95 (d, 1H), 7.55 (d, 2H), 7.2 (m, 5H), 7.05 (t, 1H), 5.25 (s, 1H), 3.4 (s, b, 2H), 2.65 (d, b, 2H), 2.1 (d, b, 4H), 1.75 (m, 2H).

Step 2:

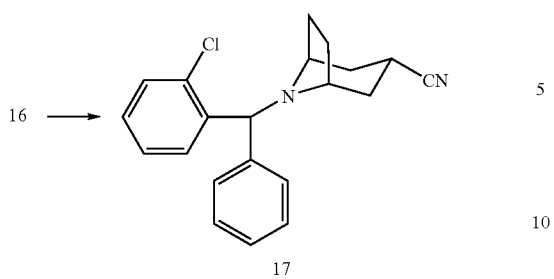

17

Compound 17 was prepared according to the procedure of Example 1, Step 5, using 16, potassium tert-butoxide and tosylmethyl isocyanide. $^1$H NMR (CDCl$_3$) δ 7.9 (d, 1H), 7.45 (d, 2H), 7.25 (m, 5H), 7.05 (t, 1H), 5.0 (s, 1H), 3.15 (s, b, 2H), 2.7 (m, 1H), 2 (m, 4H), 1.65 (m, 2H), 1.25 (d, 2H).

Step 3:

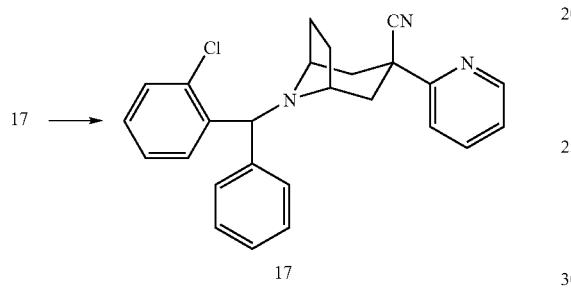

17

Compound 18 was prepared according to the procedure of Example 2, Step 1, using 17, NaHMDS and 2-bromopyridine. LC/ESI-MS: m/z 414 (C$_{26}$H$_{24}$ClN$_3$.H$^+$).

Step 4:

The procedure of Example 6, Step 2, was used with 18 and conc. HCl to give the title compound. LC/ESI-MS: m/z 389. (C$_{25}$H$_{25}$ClN$_2$.H$^+$).

EXAMPLE 15

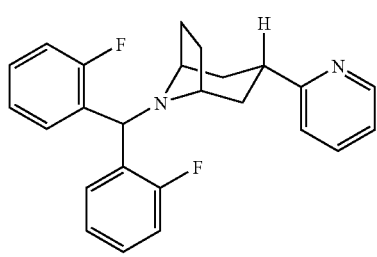

Step 1:

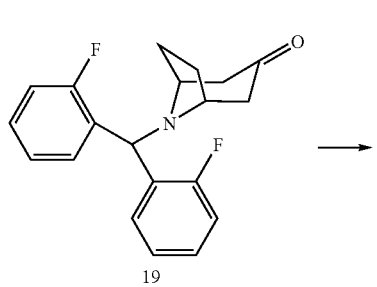

19

-continued

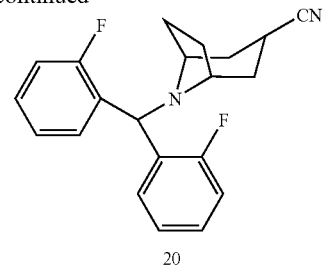

20

Compound 20 was prepared according to the procedure of Example 1, Step 5, using 19, tosylmethyl isocyanide and potassium tert-butoxide in anhydrous 1,2-dimethoxyethane and absolute EtOH. ESI-MS: m/z 339 (C$_{21}$H$_{20}$F$_2$N$_2$.H$^+$).

Step 2:

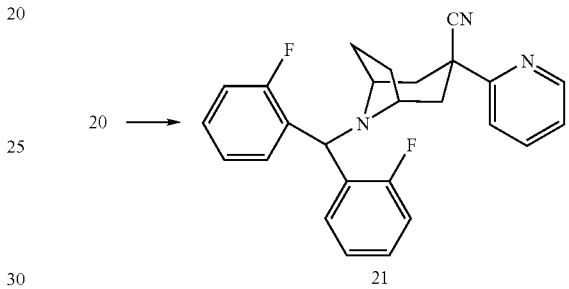

21

Compound 21 was prepared according to the procedure of Example 2, Step 1, using 20, NaHMDS and 2-bromopyridine in THF. ESI-MS: m/z 416 (C$_{26}$H$_{23}$F$_2$N$_3$.H$^+$).

Step 3:

Using the procedure of Example 2, Step 2, with 21 and NaOH in ethylene glycol, the title compound was prepared. LC/ESI-MS m/z=391 (C$_{25}$H$_{24}$F$_2$N$_2$.H$^+$)

EXAMPLE 16

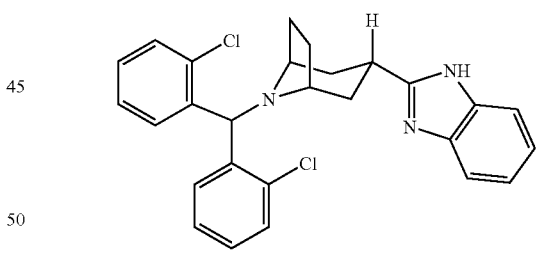

Step 1:

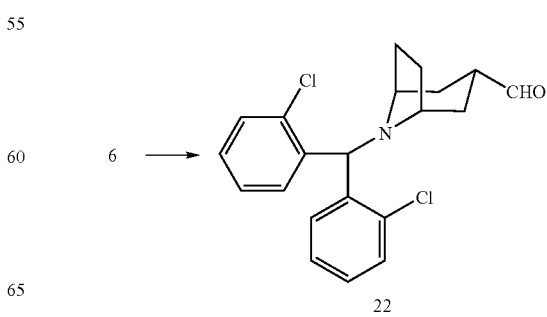

22

A solution of 6 (2 g) was added to DIBAL/toluene (7.5 ml, 1.5 M) at 0° C. The mixture was slowly warmed to rt and then stirred at 50° C. for 3 h, quenched with MeOH and H₂O at 0° C., filtered, extracted with EtOAc, dried (MgSO₄), filtered and concentrated. Purification of the residue by SiO₂ chromatography (5% EtOAc/hexane) gave 22. $^1$H NMR (CDCl₃) δ 9.6 (s, 1H), 7.75, d, 2H), 7.2 (m, 4H), 7.1 (t, 2H), 5.4 (s, 1H), 3.1 (s, br, 1H), 2.5 (m, 1H), 2.2 (m, 2H), 1.75 (t, 2H), 1.5 (m, 4H). LC/ESI-MS m/z=374 ($C_{21}H_{21}Cl_2NO.H^+$)

Step 2:

To a solution of 22 (410 mg) in EtOH was added 1,2-diaminobenzene (119 mg) and NaHSO₃ (2.3 ml, 40% in H₂O). The mixture was stirred at reflux for 3 h, concentrated, then partitioned between CH₂Cl₂ and water. The CH₂Cl₂ solution was dried (MgSO₄), filtered and concentrated. Purification of the residue by SiO₂ chromatography gave the title compound. LC/ESI-MS m/z=462 ($C_{27}H_{25}Cl_2N_3.H^+$)

EXAMPLE 17

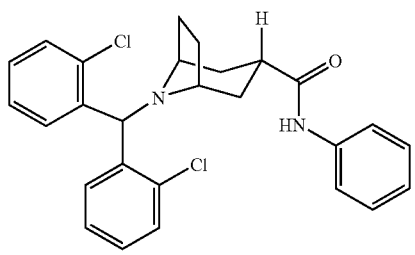

Step 1:

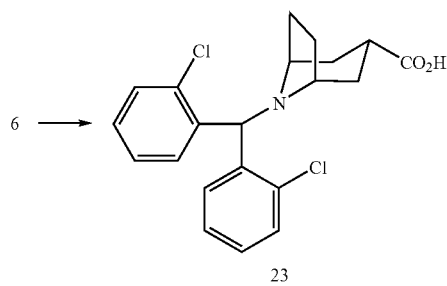

Compound 6 (1 g) was dissolved in conc. HCl and then kept at 0° C. for 3 days. The solution was then heated to 80° C. for 2 h, cooled to rt, and evaporated to dryness. Water was added and the solution was adjusted to pH 7 using 1 N NaOH solution. The aqueous solution was partitioned with EtOAc. The organic layer was dried over Na₂SO₄, filtered, and concentrated to give 23 (970 mg), which was directly used in the next step. ESI-MS: m/z 390 ($C_{21}H_{21}Cl_2NO_2.H^+$).

Step 2:

To a solution of 23 (21.5 mg, 0.055 mmol) in DMF at rt was added EDCI (15.9 mg, 0.0827 mmol) and HOBT (10.4 mg, 0.077 mmol) in DMF and aniline (5.6 mg, 0.06 mmol) in DMF. Et₃N (26 μl, 0.187 mmol) was then added. The reaction mixture was stirred at rt overnight. Water and EtOAc were added to the reaction mixture. The organic layer was dried over Na₂SO₄, filtered, and concentrated. Purification of the residue by SiO₂ chromatography gave the title compound (11.2 mg). LC/ESI-MS: m/z 465 ($C_{27}H_{26}Cl_2N_2O.H^+$).

EXAMPLE 18

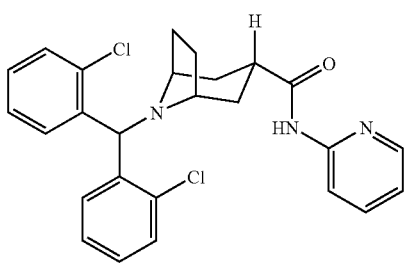

To a mixture of 23 (118 mg, 0.303 mmol) and 2-aminopyridine (55 mg, 0.58 mmol) in anhydrous CH₂Cl₂ was added EDCI (118 mg, 0.76 mmol) and DMAP (15 mg, 0.123 mmol) at rt under N₂. The reaction mixture was stirred at rt overnight. The solvent was evaporated in vacuo, and ether and water were added to the residue. The organic layer was dried over Na₂SO₄, filtered and concentrated. Purification of the residue by SiO₂ chromatography gave the title compound (97 mg). LC/ESI-MS: m/z 466 ($C_{26}H_{25}Cl_2N_3O.H^+$).

EXAMPLE 19

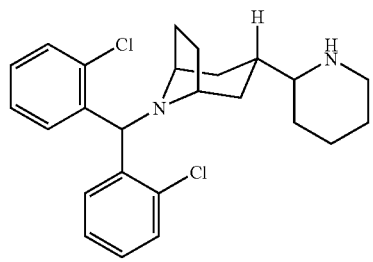

PtO₂ (40 mg) was added to a solution of Example 2 (200 mg) in CH₂Cl₂. The mixture was stirred at rt under 1 atm H₂ environment through a balloon for ~24 h, filtered and concentrated. Purification of the residue by SiO₂ chromatography gave the title compound (~190 mg). LC/ESI-MS: m/z 429 ($C_{25}H_{30}Cl_2N_2.H^+$).

EXAMPLE 20

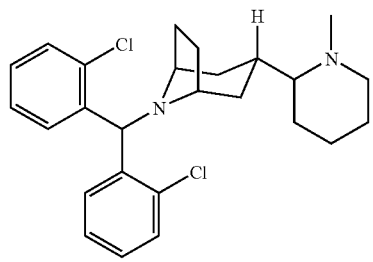

A suspension of Example 19 (30 mg) in formic acid (100 μl) and 37% aq. formaldehyde (200 μl) was stirred and heated at 70° C. for ~7 h. The mixture was evaporated to dryness, and then distributed to EtOAc and 1 N NaOH solution. The organic layer was dried over Na$_2$SO$_4$, filtered and concentrated. Purification of the residue by SiO$_2$ chromatography gave the title compound (17.8 mg). LC/ESI-MS: m/z 443 (C$_{26}$H$_{32}$Cl$_2$N$_2$.H$^+$).

EXAMPLE 21

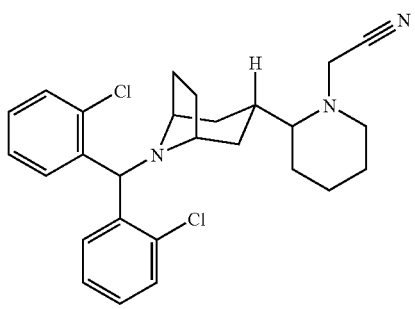

A mixture of Example 19 (55 mg, 0.128 mmol) and K$_2$CO$_3$ (53 mg, 0.385 mmol) in DMF was stirred at rt for 20 min, and then bromoacetonitrile (17.8 µl, 0.256 mmol) was added. The mixture was stirred at rt for 30 min and then heated at 60° C. overnight. The mixture was cooled to rt, quenched with water, extracted with ether, dried over MgSO$_4$, filtered and concentrated. Recrystallization of the residue gave the title compound (16 mg). LC/ESI-MS: m/z 468 (C$_{27}$H$_{31}$Cl$_2$N$_3$.H$^+$).

EXAMPLE 22

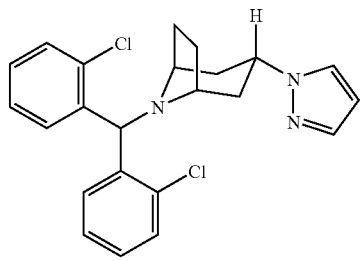

Step 1:

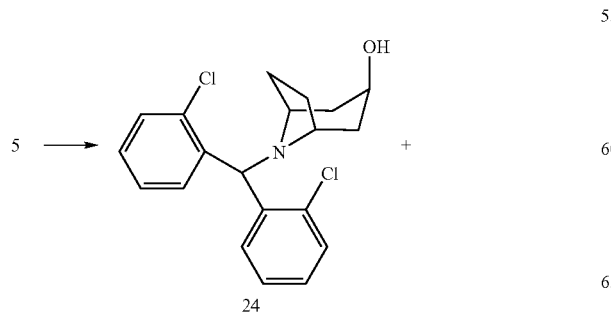

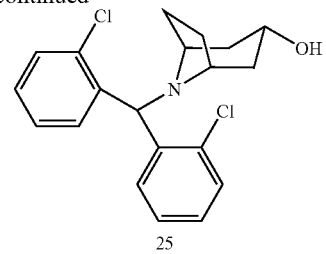

To a stirred solution of 5 (5 g) in MeOH (200 ml) was added NaBH$_4$ (0.7 g) at 0° C. The mixture was stirred at 0° C. for 2 h. The MeOH was evaporated and the resultant residue was treated with aqueous NH$_4$Cl, extracted with EtOAc, dried (MgSO$_4$), filtered and concentrated. Purification of the residue by SiO$_2$ chromatography gave compound 24 (2.54 g), LC/ESI-MS: m/z 362 (C$_{20}$H$_{21}$Cl$_2$NO.H$^+$) and compound 25 (1.71 g), LC/ESI-MS: m/z 362 (C$_{20}$H$_{21}$Cl$_2$NO.H$^+$).

Step 2:

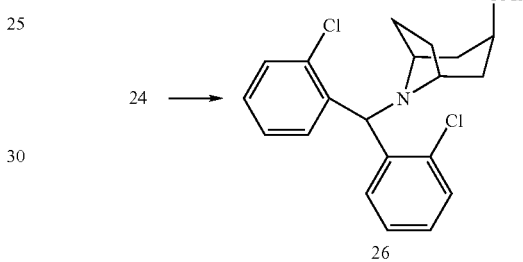

To a stirred solution of 24 (1.38 g) in CH$_2$Cl$_2$ (35 ml) was added Et$_3$N (0.64 ml) and CH$_3$SO$_2$Cl (0.36 ml) at 0° C. The mixture was stirred at 0° C. for 3.5 h, quenched with water, extracted with CH$_2$Cl$_2$, dried (Na$_2$SO$_4$), filtered and concentrated to give 26. LC/ESI-MS: m/z=440 (C$_{21}$H$_{23}$Cl$_2$NO$_3$S.H$^+$). The crude product was used in the next reaction without further purification.

Step 3:

To a solution of 26 (286 mg) in DMF (3 ml) was added NaH (60% in mineral oil, 39 mg) at 0° C. The mixture was stirred at 0° C. for 10 min., warmed to rt, then pyrazole was added and the mixture stirred at 60° C. overnight. The reaction was quenched with aqueous NH$_4$Cl, and the mixture extracted with EtOAc, dried over Na$_2$SO$_4$, and purified by preparative TLC to give the title compound. LC/ESI-MS: m/z=412 (C$_{23}$H$_{23}$Cl$_2$N$_3$.H$^+$).

EXAMPLE 23

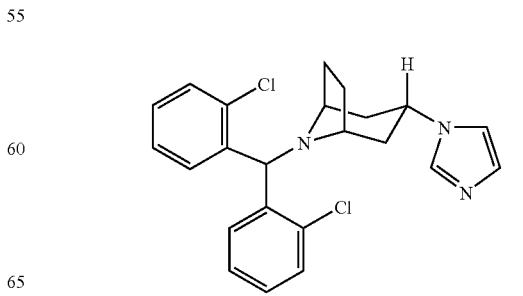

The title compound was prepared according to the procedure of Example 22, Step 3, using 26 and imidazole. ESI-MS: m/z=412 ($C_{23}H_{23}Cl_2N_3.H^+$).

EXAMPLES 24 AND 25

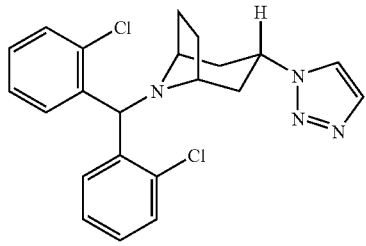
Ex. 24

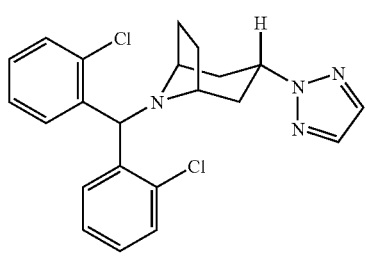
Ex. 25

A mixture of the title compounds was prepared according to the procedure of Example 22, Step 3, using 26 and 1,2,3-triazole. Purification of the mixture by SiO$_2$ chromatography (EtOAc/hexane) gave Example 24, LC/ESI-MS: m/z 413 ($C_{22}H_{22}Cl_2N_4.H^+$) and Example 25, LC/ESI-MS: m/z 413 ($C_{22}H_{22}Cl_2N_4.H^+$).

EXAMPLE 26

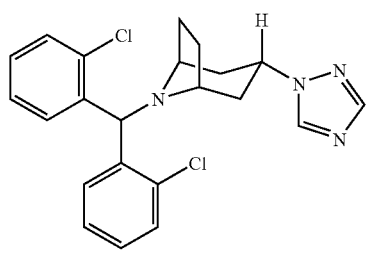

The title compound was prepared according to the procedure of Example 22, Step 3, using 26 and 1,2,4-triazole. ESI-MS: m/z=413 ($C_{22}H_{22}Cl_2N_4.H^+$).

EXAMPLE 27

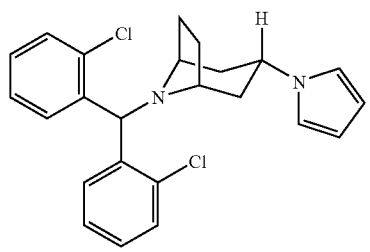

The title compound was prepared according to the procedure of Example 22, Step 3, using 26 and pyrrole. ESI-MS: m/z=411 ($C_{24}H_{24}Cl_2N_2.H^+$).

EXAMPLE 28

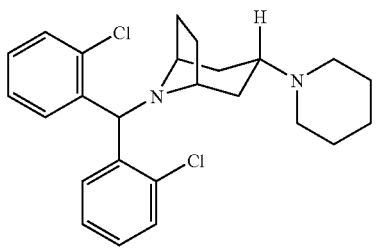

The title compound was prepared according to the procedure of Example 22, Step 3, using 26 and piperidine. ESI-MS: m/z=429 ($C_{25}H_{30}Cl_2N_2.H^+$).

EXAMPLE 29

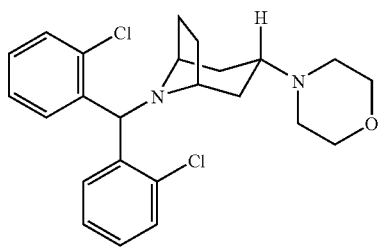

The title compound was prepared according to the procedure of Example 22, Step 3, using 26 and morpholine. ESI-MS: m/z=431 ($C_{24}H_{28}Cl_2N_2O.H^+$).

EXAMPLES 30 AND 31

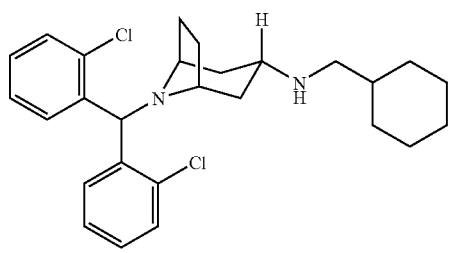
Ex. 30

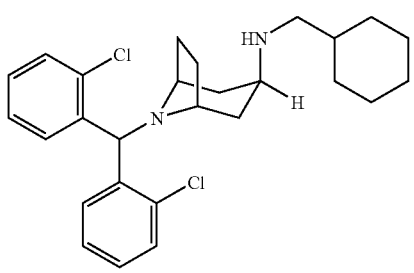
Ex. 31

To a solution of aminomethylcyclohexane (39 μl, 0.3 mmol) and 5 (72 mg) in THF was added NaBH$_3$CN (32 mg, 0.5 mmol). The mixture was stirred for ~2 h and then HOAc (60 mg, 1 mmol) was added. The mixture was stirred overnight at rt, water and 1N NaOH were added, and the mixture was extracted with ether and concentrated. Purification of the residue by SiO$_2$ chromatography gave Example 30, LC/ESI-MS: m/z 457 (C$_{27}$H$_{34}$Cl$_2$N$_2$.H$^+$) and Example 31, LC/ESI-MS: m/z 457 (C$_{27}$H$_{34}$Cl$_2$N$_2$.H$^+$).

EXAMPLE 32

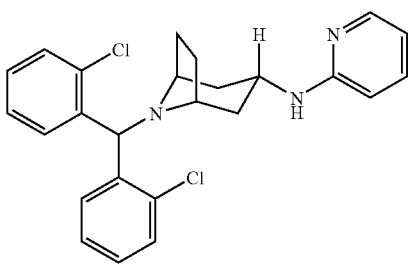

Step 1:

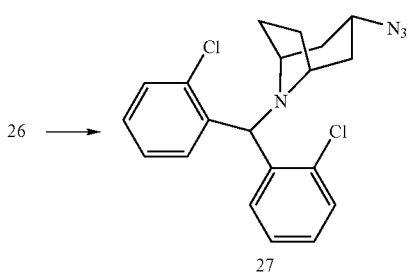

26 →

A mixture of 26 (1.68 g) and lithium azide (225 g) in DMF (5 ml) was stirred at rt for 24 h, quenched with NH$_4$Cl (aq.), extracted with EtOAc, dried over Na$_2$SO$_4$ and concentrated. Purification of the residue by SiO$_2$ chromatography gave 27. LC/ESI-MS: m/z=387 (C$_{20}$H$_{20}$Cl$_2$N$_4$.H$^+$).
Step 2:

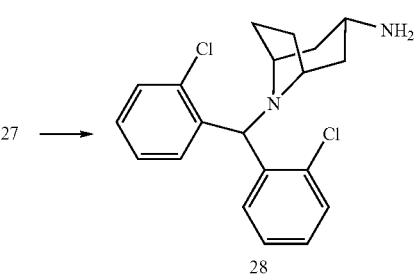

27 →

A mixture of 27 (895 mg) and Lindlar catalyst (90 mg) in 1:1 MeOH and EtOAc (20 ml) in the presence of NH$_3$ in MeOH (2M, 1 ml) was stirred under H$_2$ at 1 atm for 2 h. The mixture was filtered and concentrated to give 28. LC/ESI-MS: m/z=361 (C$_{20}$H$_{22}$Cl$_2$N$_2$.H$^+$).
Step 3:

A mixture of 28 (223 mg) and DIPEA (80 mg) in 2-fluoropyridine was stirred at 130° C. for 36 h. The mixture was concentrated, treated with NH$_4$Cl (aq.), extracted with EtOAc, dried and concentrated. Purification of the residue by SiO$_2$ chromatography gave the title compound (163 mg). ESI-MS: m/z=438 (C$_{25}$H$_{25}$Cl$_2$N$_3$.H$^+$).

EXAMPLE 33

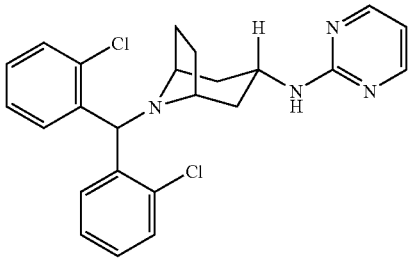

NaH (14 mg, 60% in mineral oil) was added to a solution of 28 (103 mg) in DMF at 0° C. The mixture was warmed to rt, 2-chloropyrimidine (65 mg) was added, and the mixture was heated to 60° C. for 0.5 h, then stirred at rt overnight. The mixture was quenched with NH$_4$Cl (aq.), extracted with CH$_2$Cl$_2$, dried over Na$_2$SO$_4$, filtered and concentrated. Purification of the residue by SiO$_2$ preparative thin layer chromatography (20% EtOAc/hexane) gave the title compound (16 mg). LC/ESI-MS: m/z=439 (C$_{24}$H$_{24}$Cl$_2$N$_4$.H$^+$).

EXAMPLE 34

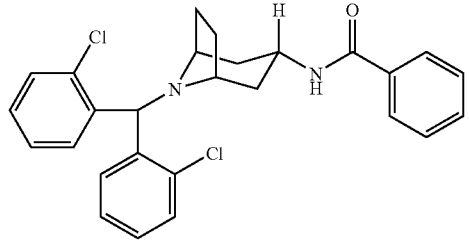

A mixture of 28 (328 mg), benzoic acid (122 mg), EDC (175 mg), and HOBT (123 mg) in DMF (2 ml) was stirred at rt overnight. The mixture was quenched with water, extracted with EtOAc, dried over MgSO$_4$ and concentrated. Purification of the residue by SiO$_2$ chromatography (0~20% EtOAc/hexane) gave the title compound. LC/ESI-MS: m/z=465 (C$_{27}$H$_{26}$Cl$_2$N$_2$O.H$^+$).

EXAMPLE 35

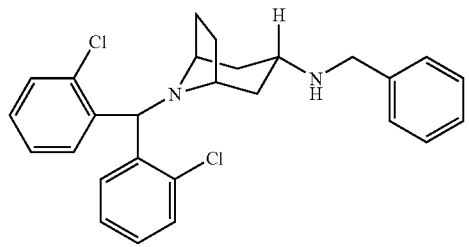

BH$_3$.THF (1.4 ml, 1M) was added to a solution of Example 34 (258 mg) in THF. The mixture was stirred at 60° C. overnight. The mixture was concentrated, treated with water, extracted with CH$_2$Cl$_2$ and concentrated. Purification of the residue by Gilson HPLC gave the title compound (25 mg). LC/ECI-MS: m/z=451 (C$_{27}$H$_{28}$Cl$_2$N$_2$.H$^+$).

EXAMPLE 36

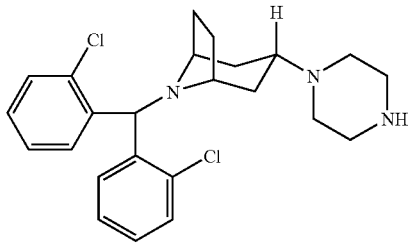

The title compound was prepared according to the procedure of Example 22, Step 3, using 26 and piperizine. ESI-MS: m/z=430 (C$_{24}$H$_{29}$Cl$_2$N$_3$.H$^+$).

EXAMPLE 37

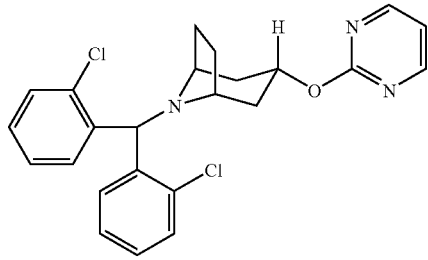

A mixture of 25 (56 mg), 2-chloropyrimidine (19 mg) and NaH (16 mg, 60% in mineral oil) in DMF (2 ml) was stirred at 0° C. for 2 h, then at rt for 3 days. The mixture was quenched with aqueous NH$_4$Cl, extracted with EtOAc, dried over Na$_2$SO$_4$ and concentrated. Purification of the residue by preparative TLC gave the title compound (36 mg). ESI-MS: m/z=440 (C$_{24}$H$_{23}$Cl$_2$N$_3$O.H$^+$).

EXAMPLE 38

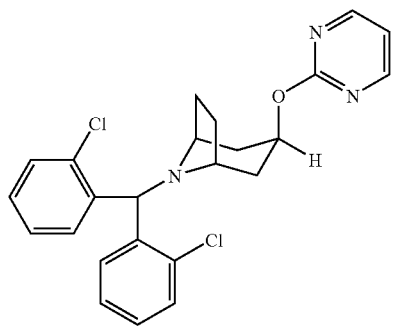

The title compound was prepared according to the procedure of Example 37 using 24, 2-chloropyrimidine and NaH. ESI-MS: m/z=440 (C$_{24}$H$_{23}$Cl$_2$N$_3$O.H$^+$).

EXAMPLE 39

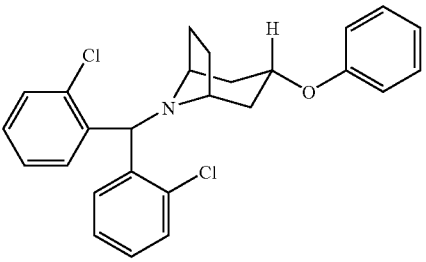

Diethyl azodicarboxylate (111 mg) in THF was added to a mixture of 24 (210 mg), phenol (55 mg) and triphenylphosphine (152 mg) in THF. The mixture was stirred at rt overnight. The mixture was concentrated, treated with hexane, filtered and concentrated. Purification of the residue by SiO$_2$ chromatography (0~20% EtOAc/hexane) gave the title compound (30 mg). LC/ESI-MS; m/z=438 (C$_{26}$H$_{25}$Cl$_2$NO.H$^+$).

EXAMPLE 40

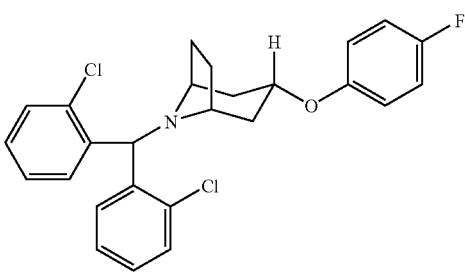

The title compound was prepared according to the procedure of Example 39 using 24, p-fluorophenol, diethyl azodicarboxylate, and triphenylphosphine. LC/ESI-MS; m/z=456 (C$_{26}$H$_{24}$Cl$_2$FNO.H$^+$).

EXAMPLE 41

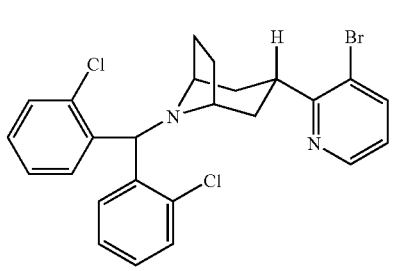

Step 1:

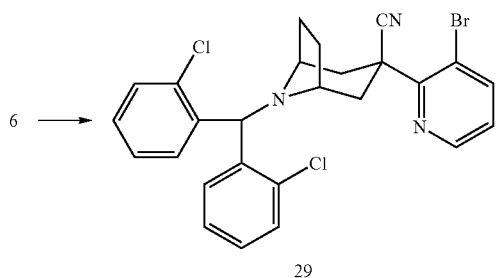

Compound 29 was prepared according to the procedure described in Example 2, Step 1, using 6, NaHMDS and 2,3-dibromopyridine. LC/ESI-MS m/z 528 ($C_{26}H_{22}BrCl_2N_3.H^+$).

Step 2:

The title compound was prepared according to the procedure described in Example 6, Step 2, using 29 and conc. HCl. LC/ESI-MS m/z 503 ($C_{25}H_{23}BrCl_2N_2.H^+$).

EXAMPLE 42

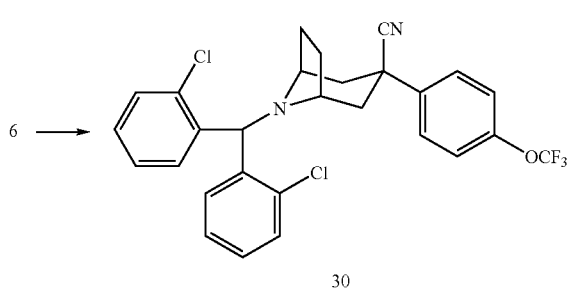

Step 1:

Compound 30 was prepared according to the procedure described in Example 13, Step 1, using 6 and 1-fluoro-4-trifluoromethoxybenzene. LC/ESI-MS m/z 531 ($C_{28}H_{23}Cl_2F_3N_2O.H^+$).

Step 2:

The title compound was prepared according to the procedure of Example 8, Step 2, using 30 and LAH. LC/ESI-MS m/z 506 ($C_{27}H_{24}Cl_2F_3NO.H^+$).

EXAMPLE 43

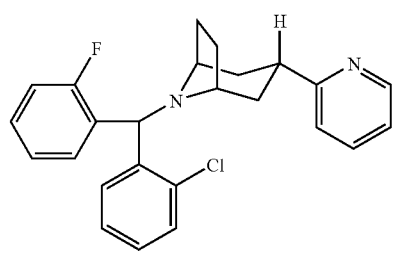

Step 1:

Example 2 →

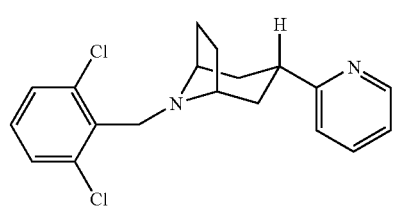

A mixture of Example 2 (4 g), Pd(OH)$_2$/C (12%, 1 g) and ammonium formate (9 g) in MeOH (100 ml) was stirred at reflux for 3 days. The mixture was filtered, concentrated, treated with water, extracted with 15% MeOH/CH$_2$Cl$_2$, dried over MgSO$_4$ and concentrated. Purification of the residue by SiO$_2$ chromatography (NH$_3$/MeOH/CH$_2$Cl$_2$) gave the title compound (1.5 g). LC/ESI-MS; m/z=189 ($C_{16}H_{12}N_2.H^+$).

Step 2:

A mixture of 31 (129 mg), chloro-(2-chlorophenyl)-(2-fluorophenyl)methane (175 mg), K$_2$CO$_3$ (380 mg) and NaI (103 mg) in CH$_3$CN (2 ml) was stirred in a sealed tube at 75° C. overnight. The mixture was cooled to rt, treated with CH$_2$Cl$_2$, filtered and concentrated. Purification of the residue by SiO$_2$ chromatography (0~10% EtOAc/hexane) gave the title compound (84 mg). LC/ESI-MS; m/z=407 ($C_{25}H_{24}ClFN_2.H^+$).

EXAMPLE 44

The title compound was prepared according to the procedure of Example 43, Step 2, using 31, 2,6-dichlorobenzylbromide and $K_2CO_3$ (508 mg). LC/ESI-MS; m/z=247 ($C_{19}H_{20}Cl_2N_2.H^+$).

EXAMPLE 45

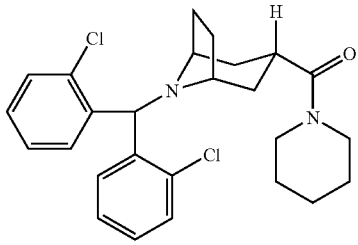

The title compound was prepared according to the procedure of Example 17 using 23 and piperidine. LC/ESI-MS: m/z 457 ($C_{26}H_{30}Cl_2N_2O.H^+$).

EXAMPLE 46

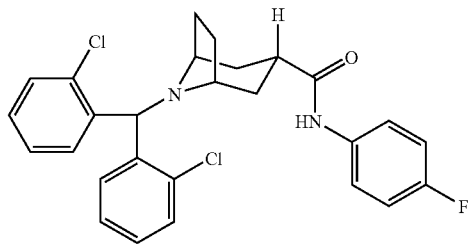

The title compound was prepared according to the procedure of Example 17 using 23 and 4-fluoroaniline. LC/ESI-MS: m/z 483 ($C_{27}H_{25}Cl_2FN_2O.H^+$).

EXAMPLE 47

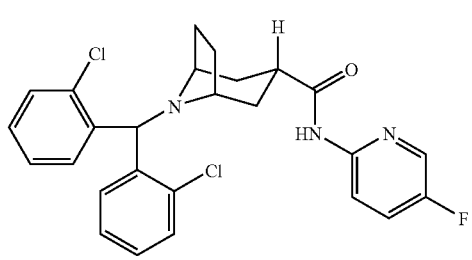

DMAP (4 mg) was added to a mixture of 23 (43 mg, 0.11 mmol), 2-amino-5-fluoropyridine (24.6 mg, 0.58 mmol) and DCC (34 mg, 0.166 mmol) in anhydrous $CH_2Cl_2$ at rt and stirred at rt for 3 days. The mixture was filtered, and the filtrate was washed with water and saturated aq. $NH_4Cl$. The organic solution was dried over $Na_2SO_4$, filtered and concentrated. Purification of the residue by $SiO_2$ chromatography (EtOAc/hexane) gave the title compound (15.5 mg). LC/ESI-MS: m/z 484 ($C_{26}H_{24}Cl_2FN_3O.H^+$).

EXAMPLE 48

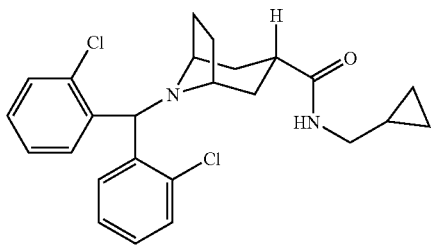

To PS-EDC resin (45 mg, 0.0615 mmol) in a cartridge was added 23 (8 mg, 0.0205 mmol) and HOBt (4.2 mg, 0.031 mmol) in 1 ml $CH_3CN$-THF (3:2). A solution of cyclopropanemethylamine in $CH_3CN$ (1 M, 45 µl, 0.045 mmol) was then added to the mixture. The cartridge was capped and shaken overnight. The mixture was treated with PS-isocyanate (40 mg, ~0.0615 mmol), PS-trisamine resins (30 mg, 0.123 mmol) and 0.5 ml $CH_3CN$-THF (3:2). The cartridge was capped and shaken for 6 h. The mixture was filtered and rinsed twice with $CH_3CN$, and the filtrate was concentrated to give the title compound (6.4 mg). LC/ESI-MS: m/z 443 ($C_{25}H_{28}Cl_2N_2O.H^+$).

EXAMPLE 49

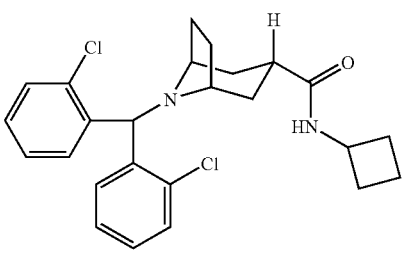

The title compound was prepared according to the procedure of Example 48 using 23 and cyclobutylamine/$CH_3CN$ (1 M). LC/ESI-MS: m/z 443 ($C_{25}H_{28}Cl_2N_2O.H^+$).

EXAMPLE 50

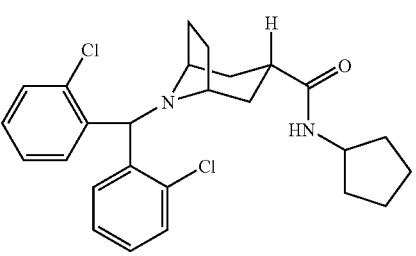

The title compound was prepared according to the procedure of Example 48 using 23 and cyclopentylamine/CH₃CN (1 M). LC/ESI-MS: m/z 457 (C$_{26}$H$_{30}$Cl$_2$N$_2$O.H$^+$).

EXAMPLE 51

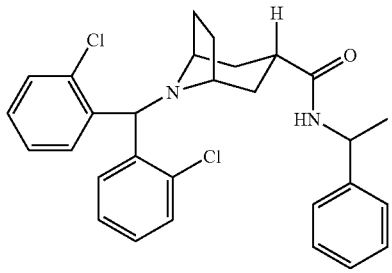

The title compound was prepared according to the procedure of Example 48 using 23 and α-methylbenzylamine/CH₃CN (1 M). LC/ESI-MS: m/z 493 (C$_{29}$H$_{30}$Cl$_2$N$_2$O.H$^+$).

EXAMPLE 52

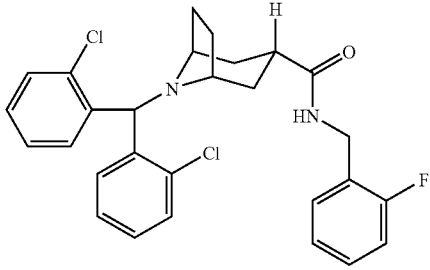

The title compound was prepared according to the procedure of Example 48 using 23 and 2-fluorobenzylamine/CH₃CN (1 M). LC/ESI-MS: m/z 497 (C$_{28}$H$_{27}$Cl$_2$FN$_2$O.H$^+$).

EXAMPLE 53

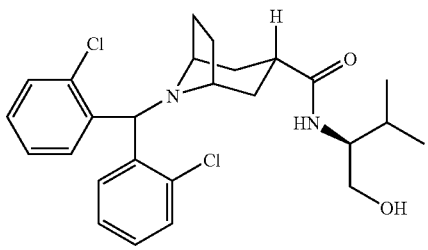

The title compound was prepared according to the procedure of Example 48 using 23 and 2-S-amino-3-methyl-1-butanol/CH₃CN (1 M). LC/ESI-MS: m/z 475 (C$_{26}$H$_{32}$Cl$_2$N$_2$O$_2$.H$^+$).

EXAMPLE 54

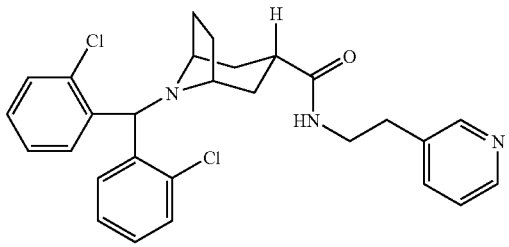

The title compound was prepared according to the procedure of Example 48 using 23 and 3-(2-aminoethyl)pyridine/CH₃CN (1 M). LC/ESI-MS: m/z 494 (C$_{28}$H$_{29}$Cl$_2$N$_3$O.H$^+$).

EXAMPLE 55

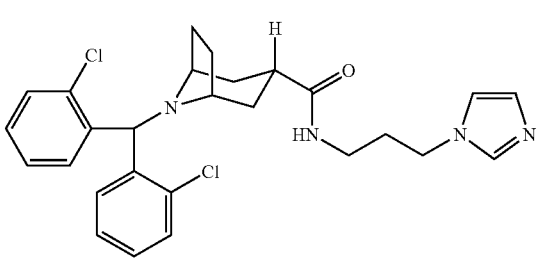

The title compound was prepared according to the procedure of Example 48 using 23 and N-(3-aminopropyl)imidazole/CH₃CN (1 M). LC/ESI-MS: m/z 497 (C$_{27}$H$_{30}$Cl$_2$N$_4$O.H$^+$).

EXAMPLE 56

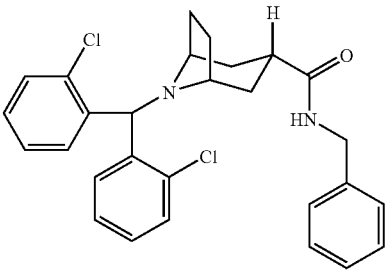

To PS-EDC resin (45 mg, 0.0615 mmol) in a cartridge was added 23 (8 mg, 0.0205 mmol) in 1 ml CH₃CN-THF (3:2) and HOBT (4.2 mg, 0.031 mmol) in THF (200 μl). The mixture was shaken at rt for 1 min, and then benzylamine/CH₃CN (1 M, 41 μl, 0.041 mmol) was added. The cartridge was capped and shaken overnight. The mixture was treated with PS-isocyanate (45 mg, 0.0615 mmol), PS-trisamine (40 mg, 0.123 mmol) resins and 0.5 ml CH₃CN-THF (3:2). The cartridge was capped and shaken for 6 h. The mixture was filtered and rinsed twice with CH₃CN. The filtrate was concentrated to give the title compound (5.5 mg). LC/ESI-MS: m/z 479 (C₂₈H₂₈Cl₂N₂O.H⁺).

EXAMPLE 57

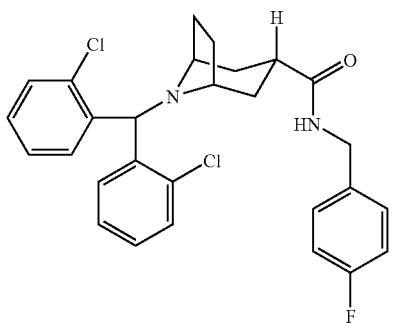

The title compound was prepared according to the procedure of Example 56 using 23 and 4-fluorobenzylamine/CH₃CN (1 M). LC/ESI-MS: m/z 497 (C₂₈H₂₇Cl₂FN₂O.H⁺).

EXAMPLE 58

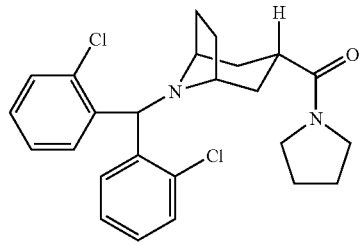

The title compound was prepared according to the procedure of Example 56 using 23 and pyrrolidine/CH₃CN (1 M). LC/ESI-MS: m/z 443 (C₂₅H₂₈Cl₂N₂O.H⁺).

EXAMPLE 59

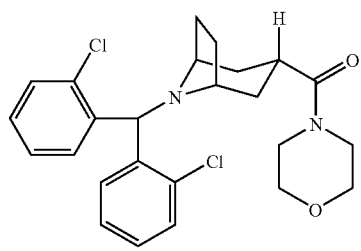

The title compound was prepared according to the procedure of Example 56 using 23 and morpholine/CH₃CN (1 M). LC/ESI-MS: m/z 459 (C₂₅H₂₈Cl₂N₂O₂.H⁺).

EXAMPLE 60

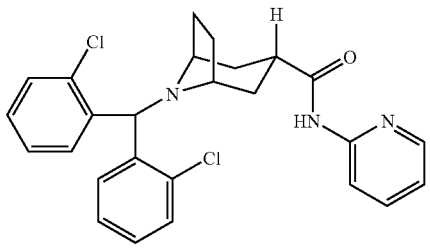

The title compound was prepared according to the procedure of Example 18 using 23 and 3-aminopyridine. LC/ESI-MS: m/z 466 (C₂₆H₂₅Cl₂N₃O.H⁺).

EXAMPLE 61

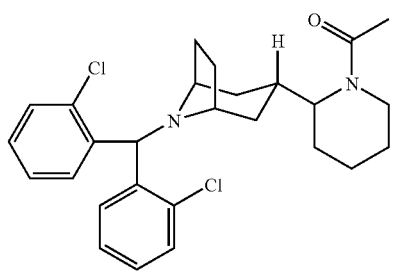

A mixture of Example 19 (34 mg) in pyridine/acetic anhydride (1:1) was stirred at 0° C. overnight and then concentrated. Purification of the residue by SiO₂ chromatography gave the title compound (13 mg). LC/ESI-MS: m/z 471 (C₂₇H₃₂Cl₂N₂O.H⁺).

EXAMPLE 62

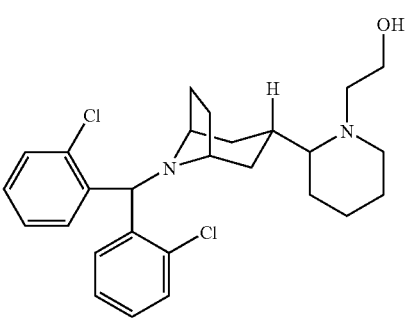

A mixture of Example 19 (40.3 mg, 0.094 mmol), K₂CO₃ (26 mg, 0.188 mmole), and 2-bromoethanol (13.3 μl, 0.188 mmol) in DMF was stirred at 50° C. for 3 days. The mixture was cooled to rt, quenched with water, and extracted with ether. The organic solution was dried over Na₂SO₄, filtered and concentrated. Purification of the residue by SiO$_2$ chromatography gave the title compound (9.4 mg). LC/ESI-MS: m/z 473 (C$_{27}$H$_{34}$Cl$_2$N$_2$O.H$^+$).

EXAMPLE 63

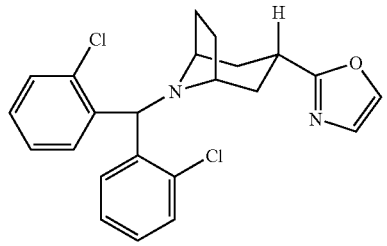

To a solution of 22 in MeOH (75 mg, 0.2 mmol) was added K$_2$CO$_3$ (83 mg, 0.6 mmol) and tosylmethyl isocyanide (39.1 mg, 0.2 mmol). The mixture was refluxed under nitrogen for 2 h, cooled to rt and extracted with EtOAc. The organic solution was dried over Na$_2$SO$_4$ and concentrated. Purification of the residue by SiO$_2$ chromatography gave the title compound (11.5 mg). LC/ESI-MS: m/z 413 (C$_{23}$H$_{22}$Cl$_2$N$_2$O.H$^+$).

EXAMPLE 64

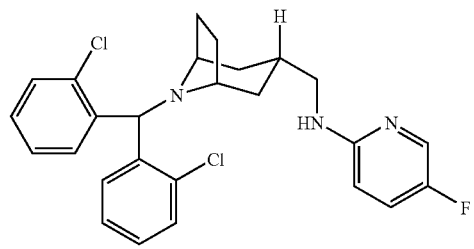

LAH/THF (1 M, 25 µl) was added to a stirred solution of Example 47 (8 mg, 0.0165 mmol) in THF at 0° C. under nitrogen. The mixture was warmed to rt, stirred overnight and H$_2$O (2 µl), 15% NaOH (6 µl), and H$_2$O (2 µl) were added sequentially. The mixture was stirred, filtered and concentrated. Purification of the residue by SiO$_2$ chromatography gave the title compound (2.5 mg). LC/ESI-MS: m/z 470 (C$_{26}$H$_{26}$Cl$_2$FN$_3$.H]$^+$).

EXAMPLE 65

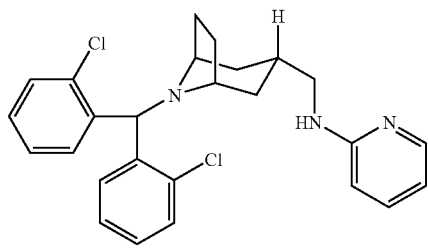

NaBH(OAc)$_3$ (32 mg, 0.15 mmol) was added to a solution of 22 (37.4 mg, 0.1 mmol) and 3-aminopyridine (9.6 mg, 0.1 mmol) in CH$_2$Cl$_2$ under nitrogen. The mixture was stirred at rt for 3 h, quenched with saturated NaHCO$_3$ solution, and extracted with EtOAc. The organic solution was dried over Na$_2$SO$_4$, filtered and concentrated. Purification of the residue by SiO$_2$ chromatography gave the title compound (19.5 mg). LC/ESI-MS: m/z 452 (C$_{26}$H$_{27}$Cl$_2$N$_3$.H$^+$).

EXAMPLE 66

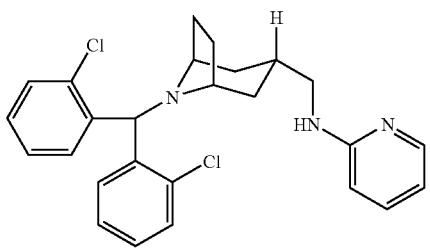

The title compound was prepared according to the procedure of Example 65 using 22, NaBH(OAc)$_3$ and 2-aminopyridine. LC/ESI-MS: m/z 452 (C$_{26}$H$_{27}$Cl$_2$N$_3$.H$^+$).

EXAMPLE 67

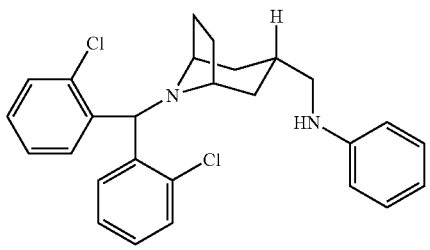

The title compound was prepared according to the procedure of Example 65 using 22, NaBH(OAc)$_3$ and aniline. LC/ESI-MS: m/z 451 (C$_{27}$H$_{28}$Cl$_2$N$_2$.H$^+$).

EXAMPLE 68

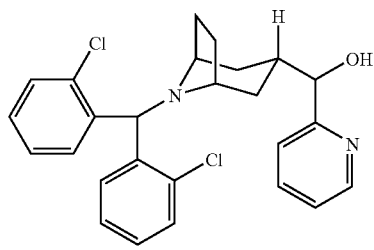

Isopropylmagnesium chloride (2M in THF, 500 µl, 1 mmol) was added to a solution of 2-bromopyridine (95.4 µl, 1 mmol) in THF dropwise at rt under nitrogen. The mixture was stirred at rt for 1.5 h, a solution of 22 in THF was added, and the mixture was stirred overnight. The reaction mixture was quenched with water, extracted with CH$_2$Cl$_2$, dried over

EXAMPLE 69

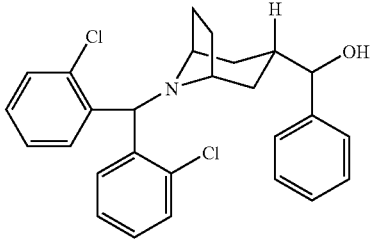

Phenylmagnesium bromide (1M in THF, 400 μl, 0.4 mmol) was added to a solution of 22 (75 mg, 0.2 mmol) in ether dropwise at −78° C. under nitrogen. The mixture was stirred at −78° C. for 5 h, quenched with saturated NH$_4$Cl solution, extracted with ether, dried over Na$_2$SO$_4$, filtered and concentrated. Purification of the residue by SiO$_2$ chromatography (EtOAc/hexane) gave the title compound (33.5 mg). LC/ESI-MS: m/z 452 ($C_{27}H_{27}Cl_2NO.H^+$).

EXAMPLE 70

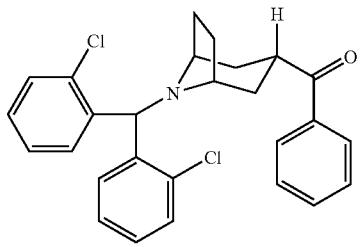

A mixture of Example 69 (22 mg, 0.049 mmol) and Dess-Martin periodinane (42 mg, 0.097 mmol) in CH$_2$Cl$_2$ was stirred at rt overnight. The mixture was diluted with ether (4 ml) and poured into a solution of saturated aqueous NaHCO$_3$ and sodium thiosulfate (126 mg, in 2 ml). The organic solution was washed with brine, dried over Na$_2$SO$_4$, and concentrated to give the title compound (18.5 mg). LC/ESI-MS: m/z 450 ($C_{27}H_{25}Cl_2NO.H^+$).

EXAMPLE 71

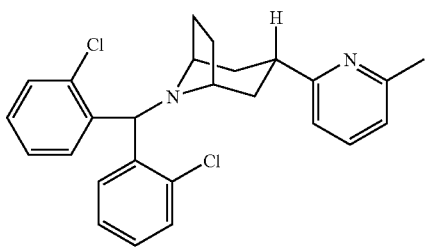

Step 1:

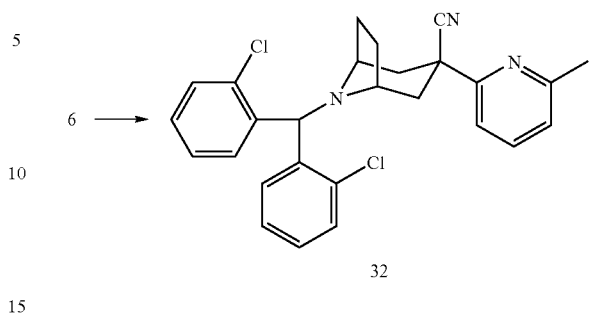

Compound 32 was prepared according to the procedure of Example 2, Step 1, using 6, NaHMDS and 2-bromo-6-methylpyridine. LC/ESI-MS: m/z 462 ($C_{27}H_{25}Cl_2N_3.H^+$).

Step 2:

The title compound was prepared according to the procedure of Example 2, Step 2, using 32 and NaOH. LC/ESI-MS: m/z 437 ($C_{26}H_{26}Cl_2N_2.H^+$).

EXAMPLE 72

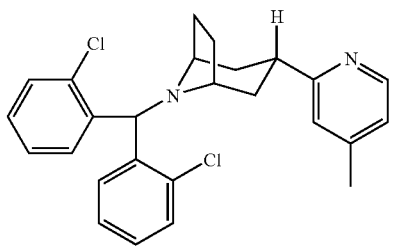

Step 1:

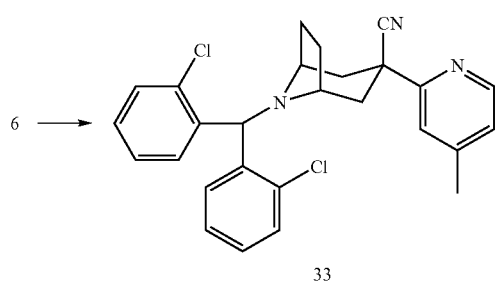

Compound 33 was prepared according to the procedure Example 2, Step 1, using 6, NaHMDS and 2-bromo-4-methylpyridine. LC/ESI-MS: m/z 462 ($C_{27}H_{25}Cl_2N_3.H^+$).

Step 2:

The title compound was prepared according to the procedure of Example 2, Step 2, using 33 and NaOH. LC/ESI-MS: m/z 437 ($C_{26}H_{26}Cl_2N_2.H^+$).

EXAMPLE 73

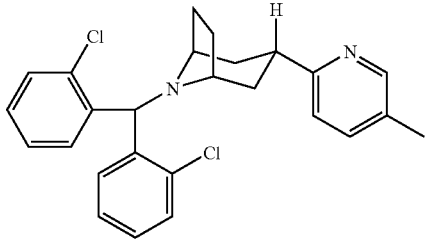

Step 1:

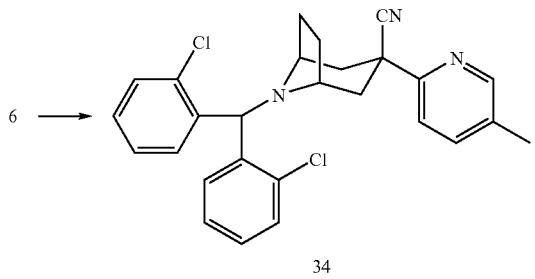

34

Compound 34 was prepared according to the procedure Example 2, Step 1, using 6, NaHMDS and 2-bromo-5-methylpyridine. LC/ESI-MS: m/z 462 ($C_{27}H_{25}Cl_2N_3 \cdot H^+$).

Step 2:

The title compound was prepared according to the procedure of Example 2, Step 2, using 34 and NaOH. LC/ESI-MS: m/z 437 ($C_{26}H_{26}Cl_2N_2 \cdot H^+$).

EXAMPLE 74

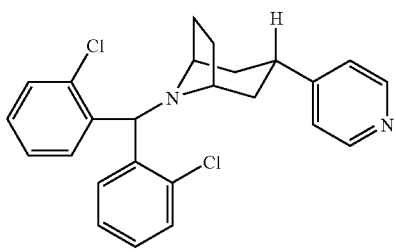

Step 1:

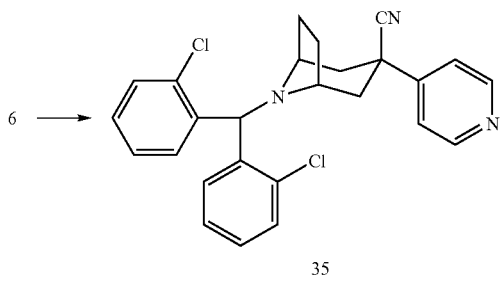

35

Compound 35 was prepared according to the procedure Example 2, Step 1, using 6, NaHMDS and 4-bromo-pyridine (derived from 4-bromo-pyridine hydrobromide). LC/ESI-MS: m/z 448 ($C_{26}H_{23}Cl_2N_3 \cdot H^+$).

Step 2:

The title compound was prepared according to the procedure of Example 2, Step 2, using 35 and NaOH. LC/ESI-MS: m/z 423 ($C_{25}H_{24}Cl_2N_2 \cdot H^+$).

The compounds of formula I exhibit greater than 50-fold selectivity over classical opioid receptors. The NOP receptor shares a high degree of homology with classical opioid receptors (i.e., μ, κ and δ), but the NOP receptor is not activated by endogenous opioids, and endogenous opioids do not activate the NOP receptor. Codeine and other opioids used as cough suppressants are known to activate the mu-opioid receptor, causing side effects such as respiratory depression, constipation, tolerance and physical dependency. NOP receptor agonists do not activate the mu-opioid receptor, and therefore are expected to result in a superior safety profile compared to opioids.

The NOP receptor agonist activity of compounds of formula I, and their effect on cough and respiration can be measured by the following tests.

Nociceptin Binding Assay

CHO cell membrane preparation expressing the NOP receptor (2 mg) was incubated with varying concentrations of [$^{125}$I][Tyr$^{14}$]nociceptin (3-500 pM) in a buffer containing 50 mM HEPES (pH7.4), 10 mM NaCl, 1 mM $MgCl_2$, 2.5 mM $CaCl_2$, 1 mg/ml bovine serum albumin and 0.025% bacitracin. In a number of studies, assays were carried out in buffer 50 mM tris-HCl (pH 7.4), 1 mg/ml bovine serum albumin and 0.025% bacitracin. Samples were incubated for 1 h at room temperature (22° C.). Radiolabelled ligand bound to the membrane was harvested over GF/B filters presoaked in 0.1% polyethyleneimine using a Brandell cell harvester and washed five times with 5 ml cold distilled water. Nonspecific binding was determined in parallel by similar assays performed in the presence of 1 μM nociceptin. All assay points were performed in duplicates of total and non-specific binding.

Calculations of Ki were made using methods well known in the art.

For compounds of this invention, Ki values were determined to be in the range of about 1 to about 500 nM, with compounds having a Ki value less than 10 nM being preferred.

Using the procedures described the *European Journal of Pharmacology*, 336 (1997), p. 233-242, the agonist activity of compounds of the invention is determined.

Cough Studies

The effects of a nociceptin agonist are evaluated in capsaicin-induced cough in the guinea pig according to the methods of Bolser et al. *British Journal of Pharmacology* (1995) 114, 735-738 (also see McLeod et al, *British Journal of Pharmacology* (2001) 132, 1175-1178). This model is a widely used method to evaluate the activity of potential antitussive drugs. Overnight fasted male Hartley guinea pigs (350-450 g, Charles River, Bloomington, Mass., USA) are placed in a 12"×14" transparent chamber. The animals are exposed to aerosolized capsaicin (300 μM, for 4 min) produced by a jet nebulizer (Puritan Bennett, Lenexa, Kans., USA) to elicit the cough reflex. Each guinea pig is exposed only once to capsaicin. The number of coughs are detected by a microphone placed in the chamber and verified by a trained observer. The signal from the microphone is relayed to a polygraph which provides a record of the number of coughs. Either vehicle (methylcellulose 1 ml/kg, p.o.) or test compound is given 2 hours before aerosolized capsaicin. The antitussive activity of baclofen (3 mg/kg, p.o.) is also tested as a positive control.

Respiratory Measurements

Studies are performed on male Hartley guinea pigs ranging in weight from 450 to 550 g. The animals are fasted overnight but given water and libitum. The guinea pigs are placed in a whole-body, head-out plethysmograph and a rubber collar is placed over the animal's head to provide an airtight seal between the guinea pig and the plethysmograph. Airflow is measured as a differential pressure across a wire mesh screen which covers a 1-in hole in the wall of the plethysmograph. The airflow signal is integrated to a signal proportional to volume using a preamplifier circuit and a pulmonary function computer (Buxco Electronics, Sharon, Conn., model XA). A head chamber is attached to the plethysmograph and air from a compressed gas source (21% $O_2$, balance $N_2$) is circulated through the head chamber for the duration of study. All respiratory measurements are made while the guinea pigs breathe this circulating air.

The volume signal from each animal is fed into a data acquisition/analysis system (Buxco Electronics, model XA) that calculates tidal volume and respiratory rate on a breath-by-breath basis. These signals are visually displayed on a monitor. Tidal volume and respiratory rate are recorded as an average value every minute.

The guinea pigs are allowed to equilibrate in the plethysmograph for 30 min. Baseline measurements are obtained at the end of this 30 min period. The guinea pigs are then removed from the plethysmograph and orally dosed with test compound (10 mg/kg, p.o.), baclofen (3 mg/kg, p.o.) or a methylcellulose vehicle placebo (2 ml/kg, p.o.). Immediately after dosing, the guinea pigs are placed into the plethysmograph, the head chamber and circulating air are reconnected and respiratory variables (tidal volume ($V_T$), respiratory rate (f) and minute volume ($MV=V_T \times f$)) are measured at 30, 60, 90 and 120 min post treatment. This study is performed under ACUC protocol #960103.

One to three compounds of formula I can be administered in the methods of this invention, preferably one.

Compounds of this invention exhibit anti-tussive activity, making them useful for suppressing coughing in mammals. For mammals treated for coughing, at least one nociceptin receptor NOP agonist of formula I may be administered along with one or more additional agents for treating cough, allergy or asthma symptoms selected from antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists. Preferably a combination of this invention comprises one compound of formula I and 1-3 additional agents, preferably 1-2 additional agents, and more preferably 1 additional agent.

Non limitative examples of antihistamines include: astemizole, azatadine, azelastine, acrivastine, brompheniramine, cetirizine, chlorpheniramine, clemastine, cyclizine, carebastine, cyproheptadine, carbinoxamine, descarboethoxyloratadine (also known as SCH-34117), doxylamine, dimethindene, ebastine, epinastine, efletirizine, fexofenadine, hydroxyzine, ketotifen, loratadine, levocabastine, mizolastine, equitazine, mianserin, noberastine, meclizine, norastemizole, picumast, pyrilamine, promethazine, terfenadine, tripelennamine, temelastine, trimeprazine and triprolidine.

Non-limitative examples of histamine $H_3$ receptor antagonists include: thioperamide, impromidine, burimamide, clobenpropit, impentamine, mifetidine, S-sopromidine, R-sopromidine, SKF-91486, GR-175737, GT-2016, UCL-1199 and clozapine. Other compounds can readily be evaluated to determine activity at $H_3$ receptors by known methods, including the guinea pig brain membrane assay and the guinea pig neuronal ileum contraction assay, both of which are described in U.S. Pat. No. 5,352,707. Another useful assay utilizes rat brain membranes and is described by West et al., "Identification of Two-$H_3$-Histamine Receptor Subtypes," *Molecular Pharmacology*, Vol. 38, pages 610-613 (1990).

The term "leukotriene inhibitor" includes any agent or compound that inhibits, restrains, retards or otherwise interacts with the action or activity of leukotrienes. Non-limitative examples of leukotriene inhibitors include montelukast [R-(E)]-1[[[1-[3-[2-(7-chloro-2-quinolinyl)-ethenyl]phenyl]-3 [2-(1-hydroxy-1-methylethyl)phenyl]propyl]thio]-methyl] cyclo-propaneacetic acid and its sodium salt, described in EP 0 480 717; 1-(((R)-(3-(2-(6,7-difluoro-2-quinolinyl)ethenyl) phenyl)-3-(2-(2-hydroxy-2-propyl)-phenyl)thio) methylcyclopropaneacetic acid, and its sodium salt, described in WO 97/28797 and U.S. Pat. No. 5,270,324; 1-(((1(R)-3(3-(2-(2, 3-dichlorothieno[3,2-b]-pyridin-5-yl)-(E)-ethenyl)phenyl)-3-(2-(1-hydroxy-1-methylethyl)phenyl) propyl)thio) methyl)cyclopropaneacetic acid, and its sodium salt, described in WO 97/28797 and U.S. Pat. No. 5,472,964; pranlukast, N-[4-oxo-2-(1H-tetrazol-5-yl)-4H-1-benzopyran-8-yl]-p-(4-phenylbutoxy)benzamide) described in WO 97/28797 and EP 173,516; zafirlukast, (cyclopentyl-3-[2-methoxy-4-[(o-tolylsulfonyl) carbamoyl]benzyl]-1-methyl-indole-5-carbamate) described in WO 97/28797 and EP 199, 543; and [2-[[2(4-tert-butyl-2-thiazolyl)-5-benzofuranyl] oxymethyl]phenyl]acetic acid, described in U.S. Pat. No. 5,296,495 and Japanese patent JP08325265 A.

The term "5-lipoxygenase inhibitor" or "5-LO inhibitor" includes any agent or compound that inhibits, restrains, retards or otherwise interacts with the enzymatic action of 5-lipoxygenase. Non-limitative examples of 5-lipoxygenase inhibitors include zileuton, docebenone, piripost, ICI-D2318, and ABT 761.

Non-limitative examples of β-adrenergic receptor agonists include: albuterol, bitolterol, isoetharine, metaproterenol, perbuterol, salmeterol, terbutaline, isoproterenol, ephedrine and epinephrine.

A non-limitative example of a xanthine derivative is theophylline.

Non-limitative examples of α-adrenergic receptor agonists include arylalkylamines, (e.g., phenylpropanolamine and pseudephedrine), imidazoles (e.g., naphazoline, oxymetazoline, tetrahydrozoline, and xylometazoline), and cycloalkylamines (e.g., propylhexedrine).

A non-limitative example of a mast cell stabilizer is nedocromil sodium.

Non-limitative examples of anti-tussive agents include codeine, dextromethorphan, benzonatate, chlophedianol, and noscapine.

A non-limitative example of an expectorant is guaifenesin.

Non-limitative examples of $NK_1$, $NK_2$ and $NK_3$ tachykinin receptor antagonists include CP-99,994 and SR 48968.

Non-limitative examples of $GABA_B$ agonists include baclofen and 3-aminopropyl-phosphinic acid.

Compounds of this invention are useful in treating UI or overactive bladder in mammals. At least one compound of formula I may be administered along with one or more additional agents for treating UI or overactive bladder. Agents known to treat UI or overactive bladder include muscarinic antagonists, for example darifenacin, tolterodine, solifenacin, trospium, duloxetine and temiverine, and antispasmodic and/ or anticholinergic agents such as oxybutynin and hyoscyamine. Preferably a combination of this invention comprises one compound of formula I and 1 additional agent.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably a compound of this invention is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to provide relief from pain, anxiety, depression, asthma or alcohol abuse. The compounds are non-toxic when administered within this dosage range.

When the NOP agonist of formula I is administered in combination with one or more additional agents, the compound of formula I and the additional agent(s) are preferably administered in a combined dosage form (e.g., a single tablet), although they can be administered separately. The additional agents are administered in amounts effective to provide relief from cough, allergy or asthma symptoms, preferably from about 0.1 mg to 1000 mg, more preferably from about 1 mg to 300 mg per unit dose. A typical recommended dosage regimen of the additional agent is from 1 mg to 2000 mg/day, preferably 1 to 1000 mg/day, in two to four divided doses. Typical dosage amounts of the other agents may be determined from the literature, for example in The Physicians's Desk Reference.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method of treating cough comprising administering an effective amount of a compound represented by the formula

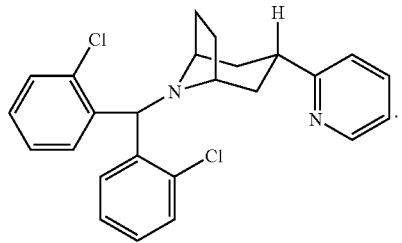

or a pharmaceutically acceptable salt thereof,
to a mammal in need of such treatment.

2. The method of claim 1, further comprising administering 1-3 additional agents selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists.

* * * * *